US008470777B2

(12) United States Patent
Gregg et al.

(10) Patent No.: US 8,470,777 B2
(45) Date of Patent: *Jun. 25, 2013

(54) PREGNANCY-INDUCED OLIGODENDROCYTE PRECURSOR CELL PROLIFERATION REGULATED BY PROLACTIN

(75) Inventors: Christopher Gregg, Cambridge, MA (US); Samuel Weiss, Calgary (CA)

(73) Assignee: Stem Cell Therapeutics Corp., Calgary, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/102,635

(22) Filed: May 6, 2011

(65) Prior Publication Data

US 2012/0064028 A1    Mar. 15, 2012

Related U.S. Application Data

(60) Division of application No. 12/419,676, filed on Apr. 7, 2009, now Pat. No. 7,964,563, and a continuation of application No. 11/535,898, filed on Sep. 27, 2006, now Pat. No. 7,534,765.

(60) Provisional application No. 60/721,025, filed on Sep. 27, 2005, provisional application No. 60/799,280, filed on May 9, 2006.

(51) Int. Cl.
*A61K 38/22* (2006.01)
*C07K 14/575* (2006.01)

(52) U.S. Cl.
USPC .......... 514/11.5; 514/7.6; 514/17.9; 514/1.1; 435/377

(58) Field of Classification Search
None
See application file for complete search history.

(56) References Cited

U.S. PATENT DOCUMENTS

| | | | |
|---|---|---|---|
| 4,703,008 A | 10/1987 | Lin | |
| 4,767,628 A | 8/1988 | Hutchinson | |
| 4,801,575 A | 1/1989 | Pardridge | |
| 4,902,680 A | 2/1990 | Aroonasakul | |
| 5,023,252 A | 6/1991 | Hseih | |
| 5,128,242 A | 7/1992 | Arimura et al. | |
| 5,198,542 A | 3/1993 | Onda | |
| 5,208,320 A | 5/1993 | Kitada et al. | |
| 5,231,178 A | 7/1993 | Holtz et al. | |
| 5,268,164 A | 12/1993 | Kozarich et al. | |
| 5,326,860 A | 7/1994 | Onda et al. | |
| 5,441,868 A | 8/1995 | Lin | |
| 5,473,054 A | 12/1995 | Jameson et al. | |
| 5,505,206 A | 4/1996 | Walloch | |
| 5,506,107 A | 4/1996 | Cunningham et al. | |
| 5,521,069 A | 5/1996 | Onda et al. | |
| 5,527,527 A | 6/1996 | Friden | |
| 5,547,935 A | 8/1996 | Mullenbach | |
| 5,547,993 A | 8/1996 | Miki | |
| 5,559,143 A | 9/1996 | McDonald et al. | |
| 5,614,184 A | 3/1997 | Sytkowski et al. | |
| 5,621,080 A | 4/1997 | Lin | |
| 5,623,050 A | 4/1997 | Kitada et al. | |
| 5,686,416 A | 11/1997 | Kozarich et al. | |
| 5,723,115 A | 3/1998 | Serrero | |
| 5,750,376 A | 5/1998 | Weiss et al. | |
| 5,753,506 A | 5/1998 | Johe | |
| 5,773,569 A | 6/1998 | Wrighton et al. | |
| 5,795,790 A | 8/1998 | Shinstine et al. | |
| 5,801,147 A | 9/1998 | Kitada et al. | |
| 5,833,988 A | 11/1998 | Friden | |
| 5,837,460 A | 11/1998 | Von Feldt et al. | |
| 5,851,832 A | 12/1998 | Weiss et al. | |
| 5,877,169 A | 3/1999 | Simpkins | |
| 5,885,574 A | 3/1999 | Elliott | |
| 5,977,307 A | 11/1999 | Friden et al. | |
| 5,980,885 A | 11/1999 | Weiss et al. | |
| 5,995,346 A | 11/1999 | Schick et al. | |
| 6,015,555 A | 1/2000 | Friden | |
| 6,017,533 A | 1/2000 | Moro et al. | |
| 6,048,971 A | 4/2000 | Sytkowski et al. | |
| 6,165,783 A | 12/2000 | Weiss et al. | |
| 6,191,106 B1 | 2/2001 | Mullenbach et al. | |
| 6,239,105 B1 | 5/2001 | Brewitt | |
| 6,242,563 B1 | 6/2001 | Dong | |
| 6,294,346 B1 | 9/2001 | Weiss et al. | |
| 6,329,508 B1 | 12/2001 | Friden | |
| 6,333,031 B1 | 12/2001 | Olsson et al. | |
| 6,376,218 B1 | 4/2002 | Hsu et al. | |
| 6,395,546 B1 | 5/2002 | Zobel et al. | |
| 6,399,316 B1 | 6/2002 | Onda et al. | |
| 6,413,952 B1 | 7/2002 | Luengo et al. | |
| 6,429,186 B1 | 8/2002 | Fuh et al. | |

(Continued)

FOREIGN PATENT DOCUMENTS

| | | |
|---|---|---|
| CA | 2175992 | 5/1995 |
| CA | 2353553 | 6/2000 |

(Continued)

OTHER PUBLICATIONS

Aberg, M.A.I. et al., "Peripheral Infusion of IGF-I Selectively Induces Neurogenesis in the Adult Rat Hippocampus," J of Neuro., vol. 20, No. 8, pp. 2896-2903 (2000).
Abramsky, O. et al., "Suppressive Effect of Pregnancy on Ms and EAE," Prog. Clin. Biol. Res., pp. 399-406 (1984).
Al-Hader et al., "Fetal rat brains contain luteinizing hormone/human chorionic gonadotropin receptors," Early Pregnancy Biol. And Med. 3:323-9 (1997).
Ai-Hader et al., "Neurons from fetal rat brain contains functional luteinizing hormone/chorionic gonadotropin receptors," Bio. Reprod. 56:1071-6 (1997).
Ai-Hader et al., "Novel expression of functional luteinizing hormone/chorionic gonadotropin receptors in cultured glial cells from neonatal rat brains," Bio. Reprod. 56:501-507 (1997).
Allen, J.S. et al., "Sexual dimorphism and asymmetries in the gray-white composition of the human cerebrum," NeuroImage, vol. 18, pp. 880-894 (2003).

(Continued)

*Primary Examiner* — Daniel C Gamett
(74) *Attorney, Agent, or Firm* — Meunier Carlin & Curfman, LLC

(57) ABSTRACT

The present invention relates to a method to increase oligodendrocytes and oligodendrocyte precursor cells through administration of prolactin or a prolactin inducing agent.

16 Claims, 13 Drawing Sheets

U.S. PATENT DOCUMENTS

| | | | |
|---|---|---|---|
| 6,551,618 | B2 | 4/2003 | Baird et al. |
| 6,618,698 | B1 | 9/2003 | Beausoleil et al. |
| 6,680,295 | B1 | 1/2004 | Arimura |
| 6,797,264 | B1 | 9/2004 | Eriksson |
| 6,812,027 | B2 | 11/2004 | Goldman et al. |
| 7,048,934 | B2 | 5/2006 | Thompson et al. |
| 7,132,287 | B2 | 11/2006 | Rajan et al. |
| 7,393,830 | B2 | 7/2008 | Shingo et al. |
| 7,514,072 | B1 | 4/2009 | Ehrenreich et al. |
| 7,534,765 | B2 | 5/2009 | Gregg et al. |
| 2002/0098178 | A1 | 7/2002 | Brand |
| 2003/0032181 | A1 | 2/2003 | Weiss et al. |
| 2003/0049838 | A1 | 3/2003 | Thompson et al. |
| 2003/0054551 | A1 | 3/2003 | Shingo et al. |
| 2003/0054998 | A1 | 3/2003 | Shingo et al. |
| 2003/0130197 | A1 | 7/2003 | Smith-Swintosky et al. |
| 2004/0038888 | A1 | 2/2004 | Mercer et al. |
| 2004/0092448 | A1 | 5/2004 | Ohta et al. |
| 2004/0209000 | A1 | 10/2004 | Curtiss et al. |
| 2004/0209812 | A1 | 10/2004 | Renzi et al. |
| 2005/0009847 | A1 | 1/2005 | Bertilsson et al. |
| 2005/0245436 | A1 | 11/2005 | Weiss et al. |
| 2006/0089309 | A1 | 4/2006 | Tucker |
| 2006/0121007 | A1 | 6/2006 | Thompson et al. |
| 2006/0148084 | A1 | 7/2006 | Shingo et al. |
| 2007/0098698 | A1 | 5/2007 | Gregg et al. |
| 2007/0111932 | A1 | 5/2007 | Anderson |
| 2007/0179092 | A1 | 8/2007 | Ohta et al. |
| 2008/0039389 | A1 | 2/2008 | Weiss et al. |
| 2008/0181873 | A1 | 7/2008 | Shingo et al. |
| 2008/0286244 | A1 | 11/2008 | Eyink |
| 2009/0274668 | A1 | 11/2009 | Thompson et al. |
| 2010/0028361 | A1 | 2/2010 | Smith et al. |
| 2010/0047233 | A1 | 2/2010 | Smith et al. |

FOREIGN PATENT DOCUMENTS

| | | |
|---|---|---|
| CA | 2556266 | 8/2005 |
| EP | 0456279 A3 | 11/1991 |
| EP | 0467 279 A3 | 1/1992 |
| WO | WO 90 05185 | 5/1990 |
| WO | WO 93 01275 | 1/1993 |
| WO | WO 94 09119 | 4/1994 |
| WO | WO 94 10292 | 5/1994 |
| WO | WO 96 09318 | 3/1996 |
| WO | WO 96 15226 | 5/1996 |
| WO | WO 96 40231 | 12/1996 |
| WO | WO 97 48729 | 12/1997 |
| WO | WO 99 15191 | 4/1999 |
| WO | WO 99 21966 | 5/1999 |
| WO | WO 99 51272 | 10/1999 |
| WO | WO 00 05260 | 2/2000 |
| WO | WO 00 13650 | 3/2000 |
| WO | WO 00 30675 | 6/2000 |
| WO | WO 01 28574 | 4/2001 |
| WO | WO 01 59074 | 8/2001 |
| WO | WO 03 018782 | 3/2003 |
| WO | WO 03 024472 | 3/2003 |
| WO | WO 03 035475 | 5/2003 |
| WO | WO 03 040310 | 5/2003 |
| WO | WO 03 092716 | 11/2003 |
| WO | WO 2004 011021 | 2/2004 |
| WO | WO 2004 011632 | 2/2004 |
| WO | 2004 045592 | 6/2004 |
| WO | WO 2006 037233 | 4/2006 |
| WO | WO 2007 106987 | 9/2007 |
| WO | WO 2009 057111 | 5/2009 |
| WO | WO 2009 137874 | 11/2009 |

OTHER PUBLICATIONS

Anderson, M.F. et al., "Insulin-like growth factor-I and neurogenesis in the adult mammalian brain," Brain Res Dev Brain Res., vol. 134, Nos. 1-2, pp. 115-122 (2002).

Arimura, A. et al., "PACAP functions as a neurotrophic factor," Ann. NY Acad. Sci., vol. 739, pp. 228-243 (1994).

Arimura, A. et al., "Perspectives on pituitary adenylate cyclase activating polypeptide PACAP in the neuroendocrine, endocrine and nervous systems," Jap. J. Physiol., vol. 48, pp. 301-331 (1998).

Arimura, A. et al., "Tissue Distribution of PACAP as Determined by RIA: Highly Abundant in the Rat Brain Testes," Endocrinol., vol. 129, pp. 2787-2789 (1991).

Arimura, A. "Pituitary adenylate cyclase activating polypeptide PACAP: Discovery and current status of research," Regulatory Peptides, vol. 37, pp. 287-303 (1992).

Arlotta et al., "Induction to Adult Neurogensis," Annals N.Y. Acad. Sci., 991(1):229-236 (2003).

Armstrong, R.C. et al., "Absence of fibroblast growth factor 2 promotes oligodendroglial repopulation of demyelinated white matter," J Neurosci., vol. 22, No. 19, pp. 8574-8585 (2002).

Arnett, H.A. et al., "TNF-α promotes proliferation of oligodendrocyte progenitors and remyelination," Nature, vol. 4, pp. 1116-1122 (2001).

Arsenijevic & Weiss "Insulin-like Growth Factor-I (IGF-I) Recruits a Distinct Population of Embryonic Neural Stem Cells," Molecular Biology of the Cell, vol. 7 (Supp), p. 1842 (Dec. 1996).

Arsenijevic et al., "Insulin-like growth factor-I is necessary for neural stem cell proliferation and demonstrates distinct actions of epidermal growth factor and fibroblast growth factor-2," Journal of Neuroscience, 21(18):7194-7202 (2001).

Aston, C., et al., "Transcriptional profiling reveals evidence for signaling and oligodendroglial abnormalities in the temporal cortex from patients with major depressive disorder," Mol Psychiatry vol. 10, pp. 309-322 (2005).

Bambakidis, N. C. and Miller, R. H. "Transplantation of oligodendrocyte precursors and sonic hedgehog results in improved function and white matter sparing in the spinal cords of adult rats after contusion," J Spine, vol. 4, p. 16-26 (2004).

Banks, W.A. et al., "Passage of pituitary adenylate cyclase activating polypeptide 1-27 and pituitary adenylate cyclase activating polypeptide 1-38 across the blood-brain barrier," J. Pharmacol. Exp. Ther., vol. 267, No. 2, pp. 690-696 (1993).

Barron, A. et al. "Time- and Dose-Dependent Effects of Ovariectomy and Human Chorionic Gonadotropin Treatment on Beta Amyloid and Isoprostane Levels in the PS1 M146V Mouse Model of Alzheimer's Disease." p. 1-436. ICAD Jul./Aug. 2008.

Bartzokis, G., et al., "Heterogeneous age-related breakdown of white matter structural integrity: implications for cortical "disconnection" in aging and Alzheimer's disease," Neurobiol Aging, vol. 25, pp. 843-851 (2004).

Bayer, S.A., "Neuron production in the hippocampus and olfactory bulb of the adult rat brain: Addition or replacement?" Ann. NY Acad. Sci., vol. 457, pp. 163-173 (1985).

Bebo, Jr., B. F. and Dveksler, G. S., "Evidence that pregnancy specific glycoproteins regulate T-Cell function and inflammatory autoimmune disease during pregnancy," Curr. Drug Targets Inflamm. & Allergy. vol. 4, pp. 231-237 (2005).

Bebo, Jr., B.F. et al., "Low-dose estrogen therapy ameliorates experimental autoimmune encephalomyelitis in two different inbred mouse strains," J. Immunol., vol. 166, pp. 2080-2089 (2001).

Belayev, L. et al. "Neuroprotective Effect of Human Chorionic Gonadotropin in Transient Focal Cerebral Ischemia in Rats," Poster. International Stroke Conference. San Antonio, TX, Feb. 23-26, 2010.

Belayev, L. et al. "A novel neurotrophic therapeutic strategy for experimental stroke." Brain Research 1280 pp. 117-123 (2009).

Bernichtein, S., et al., S179D-human PRL, a pseudophosphorylated human PRL analog, is an agonist and not an antagonist. Endocrinology, vol. 142, No. 9, pp. 3950-3963 (2001).

Bithell et al. "Neural Stem Cells and Cell Replacement Therapy: Making the right cells," Clin. Sci. 108:13-22 (2005).

Brannvall et al, "Estrogen-receptor-dependent regulation of neural stem cell proliferation and differentiation," Mol. Cell. Neurosci. 21(3):512-20 (2002).

Brown et al, "Enriched environment and physical activity stimulate hippocampal but not olfactory bulb neurogenesis," Eur J Neurosci. 17(10):2042-2046 (2003).

Brück, W. and Stadelmann, C., "The spectrum of multiple sclerosis: new lessons from pathology," Curr Opin Neurol, vol. 18, pp. 221-224 (2005).

Buckner, R.L., "Memory and executive function in aging and AD: multiple factors that cause decline and reserve factors that compensate," Neuron, 44:195-208 (2004).

Camarillo, I. G. et al., "Prolactin receptor expression in the epithelia and stroma of the rat mammary gland," J Endocrinol, vol. 171, pp. 85-95 (2001).

Cao, Q. et al., "Functional recovery in traumatic spinal cord injury after transplantation of multineurotrophin-expressing glial-restricted precursor cells," J Neurosci, vol. 25, No. 30, pp. 6947-6957 (2005).

Carey, R.G. et al., "Pituitary Adenylate Cyclase Activating Polypeptide Antimitogenic Signaling in Cerebral Cortical Progenitors is Regulated by p57Kip2-dependent CDK2 activity," J. Neurosci., vol. 22, No. 5, pp. 1583-1591 (2002).

Cerghet, M. et al., "Proliferation and death of oligodendrocytes and myelin proteins are differentially regulated in male and female rodents," J Neurosci, vol. 26, No. 5, pp. 1439-1447 (2006).

Cerami, A. "Effects of Epoetin Alfa on the Central Nervous System," Seminars in Oncology, vol. 28, No. 2. Suppl 8, pp. 66-70 (Apr. 2001).

Chikanza, I. C. "Prolactin and neuroimmunomodulation: in vitro and in vivo observations," Ann. N. Y. Acad. Sci., vol. 876, pp. 119-130 (1999).

Choi, H.K. and Waxman, D. "Growth Hormone, but Not Prolactin, Maintains Low-Level Activation of STAT5a and STAT5b in Female Rat Liver." Endocrinology 140: 5126-5135, 1999.

Chojnacki, A. and Weiss, S., "Expression and putative function of MASH1 and MASH2 in EGF-responsive forebrain neural stem cells." Society for Neuroscience, Presentation No. 600.14. Nov. 8, 2000. (abstract).

Chojnacki, A. and Weiss, S., "Isolation of a novel platelet-derived growth factor—responsive precursor from the embryonic ventral forebrain," J. Neurosci., vol. 24, No. 48, pp. 10888-10899 (2004).

Christophe, J. "Type I Receptors for PACAP (a neuropeptide even more important than VIP?)" Biochim. Biophys. Acta, vol. 1154, pp. 183-199 (1993).

Confavreux, C. et al.,"Rate of pregnancy-related relapse in multiple sclerosis," N Engl J Med., vol. 339, No. 5, pp. 285-291 (1998).

Craig, C.G. et al., "In vivo growth factor expansion of endogenous subependymal neural precursor cell populations in adult mouse brain," J. Neurosci., vol. 16, No. 8, pp. 2649-2658 (1996).

Cramer, S. et al. "The Beta-hCG + Erythropoietin in Acute Stroke (BETAS) Study. A 3-Center, Single Dose, Open-Label, Noncontrolled, Phase IIa Safety Trial," Stroke. pp. 1-4. Published online Mar. 4, 2010.

Cunningham, B. C., et al., "High-resolution epitope mapping of hGH-receptor interactions by alanine-scanning mutagenesis," Sci., vol. 244, p. 1081-1085 (1989).

Cunningham, B.C. et al., "Receptor and antibody epitopes in human growth hormone identified by homolog-scanning mutagenesis," Sci., vol. 243, No. 4896, pp. 1330-1336 (1989).

Curtis, M. et al. "Neurogenesis in the Diseased Adult Human Brain," Cell Cycle 2:5, 428-430; Sep./Oct. 2003.

Davidoff, AW. et al., "Open labeled, uncontrolled pharmacokinetic study of a single intramuscular hCG dose in healthy male volunteers." International Journal of Clinical Pharmacology and Therapeutics, vol. 47: 1-9, Jul. 5, 2009.

Dawson, M.R.L. et al., "NG2-expressing glial progenitor cells an abundant and widespread population of cycling cells in the adult rat CNS," Mol Cell Neurosci, vol. 24, pp. 476-488 (2003).

Devito et al., "Prolactin-Stimulated Mitogenesis of Cultured Astrocytes," Endocrinologoy 130 (5): 2549-2556 (1992).

Devito, W.J., et al., "Prolactin induced experession of interleukin-1 alpha, tumor necrosis factor-alpha, and transforming growth factor-alpha in cultured astrocytes" J. Cell Biochem., vol. 57, pp. 290-298 (1995).

Dicco-Bloom et al., "The PACAP Ligand/Receptor System Regulates Cerebral Cortical Neurogenisis", Annals of the New York Academy of Sciences, 274-289 (1998).

Doetsch, Fiona et al. "Subventricular Zone Astrocytes Are Neural Stem Cells in the Adult Mammalian Brain." Cell, 97 (6), 703-716 (1999).

Dong, W. K. and Greenough W. T., "Plasticity of nonneuronal brain tissue: roles in developmental disorders," Ment Retard Dev Disabil Res. Rev., vol. 10, pp. 85-90 (2004).

Draca, S. and Levic, X. "The possible role of prolactin in the immunopathogenesis of multiple sclerosis," Med. Hypotheses, vol. 47, pp. 89-92 (1996).

Dubey et al., "Differential penetration of three anterior pituitary peptide hormones into the cerebrospinal fluid of rhesus monkeys," Life Sci. 32(16): 1857-1863 (1983).

Dulac et al., "Molecular detection of pheromone signals in mammals: from genes to behaviour," Nat. Rev. Neurosci. 4(7):551-562 (2003).

Ehrenreich et al., "Recombinant Human Erythropoietin in the Treatment of Acute Ischemic Stroke," Stroke. 2009;40:e647-e656.

Ehrenreich et al., "Erythropoeitin therapy for acute stroke is both safe and beneficial," Mol. Med. 8(8):495-505 (2002).

English translation of Heike, Toshio and Nakahata, Tatsutoshi. "Stem Cells and Self-Renewal". Japanese Journal of Cancer Chemotherapy, 28(8), 1049-1056 (2001).

English translation of Murayama, Ayako and Okano, Hideyuki. "Brain Stem Cells: The Path to Regenerative Medicine of the Brain The Identification of Neural Brain Cells and Their Application to Neurological Diseases". Brain 213(1):9-14 (2000).

English translation of Shimazaki, Takuya and Okano, Hideyuki. "1. Biochemistry of Neural Stem Cells". Experimental Medicine, 18 (9), 1264-1269 (2000).

Eriksson, P. et al., "Neurogenesis in the adult human hippocampus," Nature Medicine, vol. 4, No. 11: 1313-1317. Nov. 1998.

Faden, A. et al. "Treatment of experimental stroke: Comparison of naloxone and thyrotropin releasing hormone." Neurology; 32: 1083-7. 1982.

Faulkner, J. and Keirstead, H. S., "Human embryonic stem cell-derived oligodendrocyte progenitors for the treatment of spinal cord injury," Transpl. Immunol., vol. 15, pp. 131-142 (2005).

Fernandez-Pol, J.A., Epidermal growth factor receptor of A431 cells. Characterization of a monoclonal anti-receptor antibody noncompetitive agonist of epidermal growth factor action. J. Biol. Chem., vol. 260, No. 8, pp. 5003-5011 (1985).

Ferro, J. M. and Madureira, S. "Age-related white matter changes and cognitive impairment," J Neurol Sci., vols. 203-204, pp. 221-225 (2002).

Fields, R.D., "Myelination: an overlooked mechanism of synaptic plasticity?" Neuroscientist, vol. 11, No. 6 pp. 528-531 (2005).

Fleming, A. S. and Walsh, C., "Neuropsychology of maternal behavior in the rat: c-fos expression during mother-litter interactions," Psychoneuroendocrinology vol. 19, Nos. 5-7, pp. 429-443 (1994).

Fowler et al., "The effects of social environment on adult neurogenesis in the female prairie vole," J. Neurobiology 51(2): 115-128 (2002).

Freed, C.R. et al., "Survival of Implanted Fetal Dopamine Cells and Neurologic Improvement 12 to 46 Months After Transplantation for Parkinson's Disease," N. Engl. J. Med., vol. 327, No. 22, pp. 1549-1555 (1992).

Freeman, M.E., et al., "Prolactin: structure, function and regulation of secretion", Physiol. Rev., vol. 80, pp. 1523-1631 (2000).

Frisen et al., "Central nervous system stem cells in the embryo and adult," Cell Mol Life Sci. 54(9):935-945 (1998).

Gage, F.H. et al., "Isolation, characterization, and use of stem cells from the CNS," Annu Rev Neurosci., vol. 18, pp. 159-192 (1995).

Gage, F.H. et al., "Survival and differentiation of adult neuronal progenitor cells transplanted to the adult brain," Proc Natl Acad Sci., 92:11879-83 (1995).

Gage, F.H. et al., "Mammalian neural stem cells", Science, vol. 287, No. 5457, pp. 1433-1438 (2000).

Garber, Ken. "Stroke treatment—light at the end of the tunnel?" Nature Biotechnology 25(8): 838-840. Aug. 2007.

Gatewood, J. D. et al., "Motherhood mitigates aging-related decrements in learning and memory and positively affects brain aging in the rat," Brain Res Bull, vol. 66, pp. 91-98 (2005).

Gensert, J. M. and Goldman, J. E., "In vivo characterization of endogenous proliferating cells in adult rat subcortical white matter," GLIA, vol. 17, pp. 39-51 (1996).

Gensert, J. M. and Goldman, J. E., "Endogenous progenitors remyelinate demyelinated axons in the adult CNS," Neuron, vol. 19, pp. 197-203 (1997).

Goeddel, D.V. et al., "Direct expression in Escherichia coli of a DNA sequence coding for human growth hormone" Nature, vol. 281, No. 5732, pp. 544-548 (1979).

Goffin V. et al., "Sequence-Function Relationships within the Expanding Family of Prolactin, Growth Hormone, Placental Lactogen, and Related Proteins in Mammals," Endocrine Reviews 17, No. 4, pp. 385-410 (1996).

Gray, G.L., et al., Periplasmic production of correctly processed human growth hormone in *Escherichia coli*: natural and bacterial signal sequences are interchangeable. Gene, vol. 39, Nos. 2-3, pp. 247-254 (1985).

Gregg, C., et al. "White matter plasticity and enhanced remyelination in the maternal CNS", The Journal of Neuroscience, Feb. 21, 2007, vol. 27(8), p. 1812-1823.

Gritti et al., "Epidermal and Fibroblast Growth Factors Behave as Mitogenic Regulators for a Single Multipotent Stem Cell-Like Population from the Subventricular Region of the Adult Mouse Forebrain," J Neurosci. 19(9): 3287-3297 (1999).

Gur, R. C. et al., "Sex differences in brain gray and white matter in healthy young adults: correlations with cognitive performance," J Neurosci, 19(10):4065-4072 (1999).

Hack, M. A. et al., "Neuronal fate determinants of adult olfactory bulb neurogenesis," Nat Neurosci, vol. 8, No. 7, pp. 865-872 (2005).

Haier, R.J. et al., "The neuroanatomy of general intelligence: sex matters," Neuroimage vol. 25, pp. 320-327 (2005).

Hansel, D.E. et al., "Regulation of Olfactory Neurogenesis by Amidated Neuropeptides," J. Neurosci. Res. vol. 66, pp. 1-7 (2001).

Hashimoto, H. et al., "Altered Psychomotor Behaviors in Mice Lacking Pituitary Adenylate Cyclase-Activating Polypeptide (PACAP)," PNAS, vol. 98, No. 23, pp. 13355-13360 (2001).

Hashimoto H. et al., "Molecular Cloning and Tissue Distribution of a Receptor for Pituitary Adenylate Cyclase Activating Polypeptide," Neuron, 11:333-342 (1993).

Hirose, M. et al., "Gene expression of PACAP and its receptors in the ES cell-derived neuronal stem cells," Japanese Journal of Pharmacology, The Japanese Pharmacological Society, Kyoto, JP, vol. 88, Suppl. 1, p. 143, (2002).

Huhtaniemi et al., "Transgenic and knockout mouse models for the study of luteinizing hormone and luteinizing hormone receptor function," Mol. Cell. Endocrinol. 187(1-2):49-56 (2002).

Inzitari, D., "Leukoaraiosis: An independent risk factor for stroke?" Stroke, vol. 34, pp. 2067-2071 (2003).

Ito, A. et al., "Estrogen treatment down-regulates TNF-α production and reduces the severity of experimental autoimmune encephalomyelitis in cytokine knockout mice," J Immunol, vol. 167, pp. 542-552 (2001).

Jin et al., "Alzheimer's disease drugs promote neurogenesis," Brain Research, 1085 (1): 183-8 (2006).

Johnson, et al., "Evaluating the Role of the Hormone Prolactin in Neuroinflammation and repair associated with experimental autoimmune encephalomyelitis," EndMS Research Conference, Banff, Alberta Canada; Dec. 10-13, 2007.

Johnson, D.L., "Erythropoietin mimetic peptides and the future," Nephrol. Dial. Transplant, vol. 15, No. 9, pp. 1274-1277 (2000).

Jokinen, H. et al., "Medial temporal lobe atrophy and memory deficits in elderly stroke patients," Eur J Neurol 11:825-832 (2004).

Kandel, "Principles of Neural Science," p. 981 (1991).

Kaplan, M.S., "Neurogenesis in the 3-month Old Rat Visual Cortex," J. Comp. Neurol., vol. 195, pp. 323-338 (1981).

Karbanova et al., "Neural stem cells transplanted into intact brains as neurospheres form solid grafts composed of neurons, astrocytes and oligodendrocyte precursors," Biomed. Papers 148(2):217-220 (2004).

Karimi-Abdolrezaee, S. et al.,, "Delayed transplantation of adult neural precursor cells promotes remyelination and functional neurological recovery after spinal cord injury," J Neurosci., vol. 26, No. 13, pp. 3377-3389 (2006).

Kaushansky, K., "Hematopoietic growth factor mimetics," Ann. N.Y. Acad. Sci., vol. 938, pp. 131-138 (2001).

Keirstead, H.S. et al., "Human embryonic stem cell-derived oligodendrocyte progenitor cell transplants remyelinate and restore locomotion after spinal cord injury," J Neurosci., vol. 25, No. 19, pp. 4694-4075 (2005).

Kempermann and Gage, "Experience-dependent regulation of adult hippocampal neurogenesis: effects of long-term stimulation and stimulus withdrawal," Hippocampus, 9(3):321-332 (1999).

Kieseier, B.C. et al., "Multiple sclerosis—novel insights and new therapeutic strategies," Curr Opin Neurol., vol. 18, pp. 211-220 (2005).

Kim, J. H. and Juraska, J. M., "Sex differences in the development of axon number in the splenium of the rat corpus callosum from postnatal day 15 through 60," Brain Res. Dev. Brain Res., vol. 102, p. 77-85 (1997).

Kim, S. et al., "Estriol ameliorates autoimmune demyelinating disease: implications for multiple sclerosis," Neurology, vol. 52, pp. 1230-1238 (1999).

Kimura, C. et al., "A Novel Peptide Which Stimulates Adenylate Cyclase: Molecular Cloning and Characterization of the Ovine and Human cDNAs," Biochem. Biophys. Res. Comm., vol. 166, pp. 81-89 (1990).

Kinsley, C. H. et al., "Motherhood improves learning and memory" Nature, vol. 402, p. 137 (1999).

Kiyokawa et al., "Modulatory role of testosterone in alann pheromone release by male rats," Horm. Behav. 45(2):122-127 (2004).

Kolb et al, "Growth factor-stimulated generation of new cortical tissue and functional recovery after stroke damage to the motor cortex of rats," J Cerebral Blood Flow & Metabolism 27(5):983-7 (2007).

Kolb, B. et al., "Nerve growth factor treatment prevents dendritic atrophy and promotes recovery of function after cortical injury," Neuroscience, 76(4):1139-1151 (1997).

Konishi, Y. et al., "Trophic effect of erythropoietin and other hematopoietic factors on central cholinergic neurons into vitro and in vivo" Brain Research 609:29-35 (1993).

Kovacs, T. et al., "Olfactory Bulb in Multiple System Atrophy", Movement Disorder, vol. 18, No. 8, pp. 938-942 (2003).

Lambert, K. G. et al., "Pup exposure differentially enhances foraging ability in primiparous and nulliparous rats" Physiol. Behav., vol. 84, pp. 799-806 (2005).

Lazic et al., "Cell based therapies for disorders of the CNS," Expert Opinion on Therapeutic Patents. vol. 15, No. 10: 1361-1376 (2005).

Learish, R.D. et al., "Intraventricular transplantation of oligodendrocyte progenitors into a fetal myelin mutant results in widespread formation of myelin" Ann Neurol, 46:716-722 (1999).

Le Cotonnec, J.Y. et al., "Clinical pharmacology of recombinant human luteinizing hormone: Part II. Bioavailability of recombinant human luteinizing hormone assessed with an immunoassay and an in vitro bioassay," Fertility and Sterility vol. 69, No. 2 Feb. 1998.

Lee et al., "Pituitary Adenylyl Cyclase-Activating Polypeptide Stimulates DNA Synthesis but Delays Maturation of Oligodendrocyte Progenitors", Journal of Neuroscience, vol. 21, No. 11, pp. 3849-3859 (2001).

Lee, K. H. et al., "Effects of glial transplantation on functional recovery following acute spinal cord injury" J. Neurotrauma, vol. 22, No. 5, 575-589, (2005).

Lei et al., "Novel expression of human chorionic gonadotropin/ luteinizing hormone receptor gene in brain," Endocrinology. May 1993, 132(5). pp. 2262-2270.

Lei et al., "Neural actions of luteinizing hormone and human chorionic gonadotropin," Seminars in Reprod. Med. 19(1):103-109 (2001).

Lelievre, V. et al., "Cross-talk between PACAP and sonic hedgehog (SHH) pathways in neural stem cells, cerebellar granular progenitor cells and oligodendrocyte progenitors to control cell fate and proliferation." Regulatory Peptides, 115(1):50 (2003) (abstract).

Lelievre, V. et al., "Fibroblast growth factor-2 converts PACAP growth action on embryonic hindbrain precursors from stimulation to inhibition." Journal of Neuroscience Research, vol. 67, No. 5, pp. 566-573 (Mar. 1, 2002).

Lelievre, V. et al., "Interactive of PACAP with sonic Hedgehog on neural stem cell and oligodendrocyte progenitor proliferation." J of Neurochemistry, vol. 85, Supp 1, p. 66 (May 20, 2003).

Lennington et al., "Neural stem cells and the regulation of adult neurogenesis," Reproductive Biology and Endocrinology, vol. 1:99, 1477-7827 (2003).

Levine, J. M. et al., "The oligodendrocyte precursor cell in health and disease" Trends Neurosci., vol. 24, No. 1, pp. 39-47 (2001).

Levison, S.W. et al., "Cycling cells in the adult rat neocortex preferentially generate oligodendroglia" J Neurosci Res., vol. 57, pp. 435-466 (1999).

Lim, D.A. et al., "Noggin antagonizes BMP signaling to create a niche for adult neurogenesis," Neuron, vol. 28, pp. 713-726 (2000).

Lindholm et al., "Developmental Regulation of Pituitary Adenylate Cyclase Activating Polypeptide (PACAP) and its Receptor 1 in Rat Brain: Function of PACAP as a Neurotrophic Factor," Ann. N.Y. Acad. Sci., vol. 865, pp. 189-196 (1998).

Livnah, O., et al., "Functional mimicry of a protein hormone by a peptide agonist: the EPO receptor complex at 2.8 A.," Science, vol. 273, No. 5274, pp. 464-471 (1996).

Lledo, P.M. et al., "Adult neurogenesis and functional plasticity in neuronal circuits," Nat Rev Neurosci 7:179-193 (2006).

Lobie et al., "Growth hormone, insulin-like growth factor I and the CNS: localization, function and mechanism of action," Growth Hormone & IGF Research, S51-S56 (2000).

Love, G. et al., "Maternal experience produces long-lasting behavioral modification in the rat," Behav Neurosci., vol. 119, No. 4, pp. 1084-1096 (2005).

Lowman et al., "Mutational analysis and protein engineering of receptor-binding determinants in human placental lactogen," J. Biol. Chem. 266:10982-8 (1991).

Lu, N. et al., "Pituitary Adenylate Cyclase-Activating Polypeptide is an Autocrine Inhibitor of Mitosis in cultured Cortical Precursor Cells," Proc. Natl. Acad. Sci., 94:3357-62 (1997).

Lubetzki, C. et al., "Promoting repair in multiple sclerosis: problems and prospects," Curr Opin Neurol., vol. 18, pp. 237-244 (2005).

Luskin, "Restricted proliferation and migration of postnatally generated neurons derived from the forebrain subventricular zone," Neuron 11(1):173-189 (1993).

Lyoo, I.K. et al., "White matter hyperintensities on magnetic resonance imaging of the brain in children with psychiatric disorders," Compr Psychiatry, vol. 43, No. 5, pp. 361-368 (2002).

Ma et al., "Role of the adrenal gland and adrenal-mediated chemosignals in suppression of estrus in the house mouse: The leeboot effect revisited," Biol Reprod. 59(6):1317-1320 (1998).

Mack, C. M. et al., "Sex differences in the distribution of axon types within the genu of the rat corpus callosum," Brain Res, vol. 697, pp. 152-156 (1995).

Mannaerts, B.M.J.L. et al., "A randomized three-way cross-over study in healthy pituitary-suppressed women to compare the bioavailability of human chorionic gonadotrophin (Pregnyl) after intramuscular and subcutaneous administration," Human Reproduction vol. 13 No. 6 pp. 1461-1464, 1998.

Markianos, M. et al. "Serum and Cerebrospinal Fluid Prolactin levels in Male and Female Patients with Clinically-Isolated Syndrome or Relapsing-Remitting Multiple Sclerosis." Journal of Neuroendocrinology 2010; 22: 503-508.

Menezes et al., "The division of neuronal progenitor cells during migration in the neonatal mammalian forebrain," Mol Cell Neurosci. 6(6):496-508 (1995).

Menn, B. et al., "Origin of oligodendrocytes in the subventricular zone of the adult brain," J Neurosci., vol. 26, No. 30, pp. 7907-7918 (2006).

Minnerup et al., "The Efficacy of Erythropoietin and Its Analogues in Animal Stroke Models: A Meta-Analysis," Stroke. 40 pp. 3113-3120. 2009.

Misra et al, "Drug Delivery to the central nervous system: a review," J Pharm Pharmaceutic Sci. 6(2): 252-73 (2003).

Miyata, A. et al., "Isolation of a Novel 38 Residue-Hypothalamic Polypeptide which Stimulates Adenylate Cyclase in Pituitary Cells," Biochem. Bophys. Res. Comm. 164:567-574 (1989).

Mode, A., et al., "The human growth hormone (hgH) antagonist G120RhGH does not antagonize GH in the rat, but has paradoxical agonist activity, probably via the prolactin receptor," Endocrinology, vol. 137, No. 2, pp. 447-454 (1996).

Moderscheim, T.A.E., et al., "Prolactin is Involved in Glial Responses Following a Focal Injury to the Juvenile Rat Brain," Neuroscience 145: 963-973 (2007).

Moore, P.B. et al., "Cerebral white matter lesions in bipolar affective disorder: relationship to outcome," Br J Psychiatry, vol. 178, pp. 172-176 (2001).

Mori, E. "Impact of subcortical ischemic lesions on behavior and cognition" Ann. N. Y. Acad Sci., vol. 977, p. 141-148 (2002).

Moro, O. et al., "Maxadilan, the vasodilator from sand flies, is a specific pituitary adenylate cyclase activating peptide type I receptor agonist," J. Biol. Chem., vol. 272, No. 2, pp. 966-970 (1997).

Morrison et al., "Regulatory mechanisms in stem cell biology," Cell 88:287-298 (1997).

Morshead et al., "Postmitotic death is the fate of constitutively proliferating cells in the subependymal layer of the adult mouse brain," J Neurosci. 12(1):249-256 (1992).

Mulloy et al., "Absorption of orally administered bouline prolactin by neonatal rats," Abstract, Biol. Neonate., 36:148-53 (1979).

Nait-Oumesmar, B., et al., "Progenitor cells of the adult mouse subventricular zone proliferate, migrate and differentiate into oligodendrocytes after demyelination" Eur J Neurosci., vol. 11, pp. 4357-4366 (1999).

Neumann, I. D., "Alterations in behavioral and neuroendocrine stress coping strategies in pregnant, parturient and lactating rats," Prog. Brain Res., 133:143-152 (2001).

Nicot, A. et al., "Regulation of Neuroblast Mitosis is Determined by PACAP Receptor Isoform Expression," PNAS, vol. 98, No. 8, pp. 4758-4763 (2001).

Nilsson et al., "Enriched environment increases neurogenesis in the adult rat dentate gyrus and improves spatial memory," J Neurobiol. 39(4):569-578 (1999).

Nuñez, J. L. et al., "Myelination in the splenium of the corpus callosum in adult male and female rats," Dev Brain Res., vol. 120, pp. 87-90 (2000).

Nyberg, F. "Aging effects on growth hormone receptor binding in the brain," Exp. Gerontol, vol. 32, Nos. 4-5, pp. 521-528 (1997).

Nyberg, F., "Growth hormone in the brain: characteristics of specific brain targets for the hormone and their functional significance," Front Neuroendocrinol., vol. 21, pp. 330-348 (2000).

Ohta S. and Weiss, S., "Pituitary adenylate cyclase-activating polypeptide (PACAP) regulates forebrain neural stem cell fate in vitro and in vivo," Society for Neuroscience, vol. 329, No. 13, 2002 (abstract).

Ormandy, C. J. et al., "Null mutation of the prolactin receptor gene produces multiple reproductive defects in the mouse" Genes Dev., vol. 11, pp. 167-178 (1997).

Ostenfeld et al., "Recent Advances in Stem Cell Neurobiology," Adv. Tech. Stand. Neurosurg. 28:3-89 (2003).

Otto, C. et al., "Altered Emotional Behavior in PACAP-type-I-receptor-deficient Mice," Brain Res. Mol. Brain Res. 91(1-2):78-84 (2001).

Park, "Transplantation of neural stem cells: cellular & gene therapy for hypoxic-ischemic brain injury," Yonsei Med. J. 41(6):825-835 (2000).

Parker et al., "Expression profile of an operationally-defined neural stem cell clone," Exper. Neuro. 194:320-332 (2005).

Patil et al., "The effect of Human Chorionic Gonadotropin (HCG) on Restoration of Physiological Continuity of the Spinal Cord. A Preliminary Report," Int. Surg. 75:54-57 (1990).

Patil, "The Study of the Effect of Human Chorionic Gonadotrophic (HCG) Homlone on the Survival of Adrenal Medulla Transport in Brain. Preliminary Study," Acta Neurochirurgica 87:76-8 (1987).

Patil et al., "The Effect of Human Chorionic Gonadotropin (HCG) on Functional Recovery of Spinal Cord Sectioned Rats," Acta Neurochirurgica 69:205-18 (1983).

Patil and Nagaraj, Letter to the Editor, Neurosurgery 12(5):593-4 (1983).

Peretto et al., "The subependymal layer in rodents: a site of structural plasticity and cell migration in the adult mammalian brain," Brain Res. Bull. 49(4):221-243 (1999).

Perlow et al., "Brain Grafts Reduce Motor Abnormalities Produced by Destruction of Nigrostriatal Dopamine System," Sci., vol. 204, pp. 643-647 (1979).

Pesce, M. et al., "Pituitary adenylate cyclass-activating polypeptide (PACAP) stimulates adenylate cyclase and promotes proliferation of mouse primordial germ cells." Development (Cambridge), vol. 122, No. 1, pp. 215-221 (1996).

Peters, A. and Sethares C., "Oligodendrocytes, their progenitors and other neuroglial cells in the aging primate cerebral cortex" Cereb Cortex, 14:995-1007 (2004).

Peters, A. et al., "Effects of aging on the neuroglial cells and pericytes within area 17 of the rhesus monkey cerebral cortex" Anat Rec, vol. 229, pp. 384-398 (1991).

Peters, A. J., "The effects of normal aging on myelin and nerve fibers: a review," J Neurocytol, vol. 31, pp. 581-593 (2002).

Phelps, C.J., "Pituitary hormones as neurotrophic signals: Update on hypothalamic differentiation in genetic models of altered feedback," Proceedings of the Society for Experimental Biology and Medicine, vol. 222, No. 1, pp. 39-58, 1999.

Phelps, C.J., "Stimulatory effect of human, but not bovie, growth hormone expression on numbers of tuberoinfundibular dopaminergic neurons in transgenic mice", Endrocrinology, vol. 138, No. 7, pp. 2849-2855 (1997).

Picard-Riera, N. et al., "Experimental autoimmune encephalomyelitis mobilizes neural progenitors from the subventricular zone to undergo oligodendrogenesis in adult mice," PNAS, vol. 99, No. 20, pp. 13211-13216 (2002).

Pluchino et al, "Injection of adult neurospheres induces recovery in a chronic model of multiple sclerosis," Nature 422(6933):688-94 (2003).

Polito, A. and Reynolds, R., "NG2 expressing cells as oligodendrocyte progenitors in the normal and demyelinated adult central nervous system," Anat., 207:707-16 (2005).

Potten, C.S. and Loeffler, M., "Stem Cells: Attributes, Cycles, Spirals, Pitfalls and Uncertainties. Lessons for and from the Crypt," Development, 110:1001-1020 (1990).

Rakic, "Limits of Neurogenesis in Primates," Science 227:1054-1056 (1985).

Rao, "Multipotent and restricted precursors in the central nervous system," Anat. Rec. vol. 257(4):137-148 (1999).

Rao et al., "Human chorionic gonadotropin/luteinizing hormone receptor expression in the adult rat spinal cord," J. Neurosci. Letters 336:135-8 (2003).

Rawlings, S.R., "At the Cutting Edge PACAP, PACAP Receptors, and Intracellular Signalling," Mol. and Cellular Endocrinol., vol. 101, pp. C5-C9 (1994).

Reynolds, B.A. and Weiss, S., "Generation of Neurons and Astrocytes from Isolated Cells of the Adult Mammalian Central Nervous System," Sci., 255:1707-1710 (1992).

Reynolds et al., "Clonal and population analyses demonstrate that an EGF-responsive mammalian embryonic CNS precursor is a stem cell," Develop. Bio. 175:1-13 (1996).

Reynolds et al., "Ethanol modulation of GABA receptor-activated C I-currents in neurons of the chick, rat and mouse central nervous system," Eur. J. Pharmacol. 224(2-3): 173-181 (1992).

Rietze, R. et al., "Mitotically Active Cells that Generate Neurons and Astrocytes are Present in Multiple Regions of the Adult Mouse Hippocampus," J. Comp. Neurol., vol. 424, No. 3, pp. 397-408 (2000).

Rochefort, C., et al, "Enriched odor exposure increases the number of newborn neurons in the adult olfactory bulb and improves odor memory," J. Neurosci., vol. 22, No. 7, pp. 2679-2689 (2002).

Rodriguez-Pena, "Oligodendrocyte development and thyroid hormone," J. Neurobiol. 40(4):497-512 (1999).

Rostene, W. et al., "VIP and PAGAP via G-Protein coupled receptors are potent inducers of mouse embryonic stem cell neuronal differentiation," Regulatory Peptides, vol. 115, No. 1, p. 55. (2003).

Rubinek, T. et al. "Prolactin (PRL)-Releasing Peptide Stimulates PRL Secretion from Human Fetal Pituitary Cultures and Growth Hormone Release from Cultured Pituitary Adenomas," The Journal of Clinical Endocrinology & Metabolism. vol. 86, No. 6 pp. 2826-2830. 2001.

Sato, A. et al., "Cystine Knot of the Gonadotropin α Subunit Is Critical for Intracellular Behavior but Not for in Vitro Biological Activity," The Journal of Biological Chemistry. vol. 272, No. 29, Issue of Jul. 18, pp. 18098-18103, 1997.

Schanzer et al., "Direct Stimulation of Adult Neural Stem Cells In vitro and Neurogenesis in vivo by vascular Endothelial Growth Factor," Brain Path. 14(3):237-48 (2004).

Scharfman et al., "Increased neurogenesis and the ectopic granuae cells after intrahippocampal BDNF infusion in rats," Exp. Neuro. 192(2):348-56 (2005).

Scheepens, A. et al., "Growth Hormone as a Neuronal Rescue Factor During Recovery from CNS Injury," Neuroscience, vol. 104, No. 3, pp. 677-687 (Jun. 14, 2001).

Schlessinger, J. et al., "Crystal Structure of a Ternary FGF-FGFR-Heparin Complex Reveals a Dual Role for Heparin in FGFR Binding Dimerization," Molecular Cell, vol. 6, No. 3, pp. 743-750 (Sep. 2000).

Schradin, C. and Anzenberger G., "Prolactin, the Hormone of Paternity" News Physiol Sci., vol. 14, pp. 223-231 (1999).

Scolding, N. J. and Franklin, R. J. M., "Remyelination in demyelinating disease" Baillieres Clin Neurol., vol. 6(3), pp. 525-548 (1997).

Shimazaki, T., et al., "The ciliary neurotrophic factor leukemia inhibitory factor/gp130 receptor complex operates in the maintenance of mammalian forebrain neural stem cells," J. Neurosci. 21(19):7642-7653 (2001).

Shingo, T., et al., "Erythropoietin regulates the in vitro and in vivo production of neuronal progenitors by mammalian forebrain neural stem cells," J. Neurosci., vol. 21, No. 24, pp. 9733-9743 (2001).

Shingo, T. et al., "Pregacy-Stimulated Neurogenesis in the Adult Female Forebrain Mediated by Prolactin," Sci., vol. 229, pp. 117-120 (2003) (including Supporting Online Material (1-10 pages)).

Shingo et al., "Pregnancy-stimulated neurogenesis in the adult female forebrain mediated by prolactin," Science 299:117-120 (2003).

Shioda, J. et al., "Pleiotropic functions of PACAP in the CNS. Neuroprotection and neurodevelopment," Ann. NY Acad. Sci., vol. 1070, pp. 550-560 (2006).

Sicotte, N. L. et al., "Treatment of multiple sclerosis with the pregnancy hormone estriol," Ann Neurol., vol. 52, pp. 421-428 (2002).

Silverstone, T. et al., "Deep white matter hyperintensities in patients with bipolar depression, unipolar depression and age-matched control subjects," Bipolar Disord, vol. 5, pp. 53-57 (2003).

Sirevaag, A. M. and Greenough, W. T., "Differential rearing effects on rat visual cortex synapses. III. Neuronal and glial nuclei, boutons, dendrites and capillaries," Brain Res., vol. 424, pp. 320-332 (1987).

Sorokan, et al., "Erythropoietin mediates increased neurogenesis by embryonic CNS stem cells following a modest hypoxic insult," Society for Neuroscience Abstracts, 23(1/2):320 (1997).

Spencer, D.D. et al., "Unilateral Transplantation of Human Fetal Mesencephalic Tissue into the Caudate Nucleus of Patients with Parkinson's Disease," New Engl. J. Med., vol. 327, No. 22, pp. 1541-1548 (1992).

Stangel, M. and Hartung H-P., "Remyelinating strategies for the treatment of multiple sclerosis," Prog Neurobiol., vol. 68, pp. 361-376 (2002).

Stevens, B. et al., "Adenosine: a neuron-glial transmitter promoting myelination in the CNS in response to action potentials," Neuron, vol. 36, pp. 855-868 (2002).

Studer et al., "Enhanced proliferation, survival, and dopaminergic differentiation of CNS precursors in lowered oxygen," J. Neurosci. 201(19):7377-83 (2000).

Sturrock, R. R. "Myelination of the mouse corpus callosum," Neuropathol Appl Neurobiol., vol. 6, pp. 415-420 (1980).

Szeligo, F. and Leblond, C. P., "Response of the three main types of glial cells of cortex and corpus callosum in rats handled during suckling or exposed to enriched, control and impoverished environments following weaning," J. Comp. Neurol., vol. 172, pp. 247-263 (1977).

Tanaka, "Potential of Use of Neural Stem Cells as Stroke as a Clinical Treatment," Juntendo Med. J. 52(1);2-124 (2006).

Tanapat et al., "Estrogen stimulates a transient increase in the number of new neurons in the dentate grus of the adult female rat," J. Neurosci. 19(14):5792-801 (1999).

Tang, D. G. et al., "Long-term culture of purified postnatal oligodendrocyte precursor cells. Evidence for an intrinsic maturation program that plays out over months," J. Cell Biol., vol. 148(5): 971-984 (2000).

Tauber, H. et al., "Myelination in rabbit optic nerves is accelerated by artificial eye opening," Neuroci Lett., vol. 16, pp. 235-238 (1980).

The American Heritage Dictionary of the English Language 4th Ed., Dictionary.com/neural (2000).

Trinchard-Lugan et al., "Pharmacokinetics and pharmacodynamics of recombinant human chorionic gonadotropin in healthy male and female volunteers," Reproductive BioMed Online; www.rbmonline. comiArtic1I280, Jan. 8, 2002. vol. 4, No. 2, 106-115.

Totoiu, M. O. and Keirstead, H. S., "Spinal cord injury is accompanied by chronic progressive demyelination," J Comp Neurol., vol. 486, pp. 373-383 (2005).

Tropepe, V. et al., "Transforming growth factor-α null and senescent mice show decreased neural progenitor cell proliferation in the forebrain subependyma," J. Neurosci., vol. 17, Issue 20, pp. 7850-7859 (1997).

Van Dam et al, "Growth Hormone, insulin-like growth factor I and cognitive function in adults," Growth Horm. IGF Res. 10 (Supp B):S69-73 (2000).

Van Der Kooy and Weiss, "Why Stem Cells?" Sci. vol. 287, pp. 1439-1441 (2000).

Van Walderveen et al., "Magnetic resonance evaluation of disease activity during pregnancy in multiple sclerosis," Neurology, vol. 44, pp. 327-329 (1994).

Vaudry, D. et al., "Neurotrophic activity of pituitary adenylate cyclase-activating polypeptide on rate cerebellar cortex during development," Proc. of the Nat. Acad. of Sci., vol. 96, No. 16, pp. 9415-9420 (Aug. 3, 1999).

Vaudry, D. et al., "Pituitary adenylate cyclase-activating polypeptide and its receptors from structure to functions," Pharmacol. Rev., vol. 52, No. 2, pp. 269-324 (2000).

Voskuhl, R. R., "Hormone-based therapies in MS" Int. MS J, vol. 10, pp. 60-66 (2003).

Walker, C. D. et al., "Mother to infant or infant to mother? Reciprocal regulation of responsiveness to stress in rodents and the implications for humans," J. Psy. Neurosci. vol. 29, No. 5, pp. 364-382 (2004).

Wardlaw, J.M. et al., "Is diffusion imaging appearance an independent predictor of outcome after ischemic stroke?" Neurology, vol. 59, pp. 1381-1387 (2002).

Waschek, J.A., "Multiple actions of pituitary adenylyl cyclase activating peptide in nervous system development and regeneration," Develop. Neuro., 24:14-23 (2002).

Waschek, J.A., "VIP and PACAP Receptor-mediated actions on cell proliferation and survival," Ann. N.Y. Acad. Sci., vol. 805, pp. 290-301 (1996).

Weetman A. P., "The immunology of pregnancy," Thyroid, vol. 9, No. 7, pp. 643-646 (1999).

Wehmann, R. and Nisula, B. "Metabolic and Renal Clearance Rates of Purified Human Chorionic Gonadotropin," J. Clin Invest. 68:184-194 (1981).

Weiss et al., "Is there a neural stem cell in the mammalian forebrain?" Trends Neuro. 19:387-393 (1996).

Whittemore S.R., et al., "Mitogen and substrate differentially affect the lineage restriction of adult rat subventricular zone neural precursor cell populations," Exp. Cell. Res., vol. 252, No. 1, pp. 75-95 (Oct. 10, 1999).

Widner, H. et al., "Bilateral fetal mesencephalic grafting into two patients with parkinsonism induced by I-methyl-4-phenyl-1,2,3,6-tetrahydropyridine (MPTP)," N. Engl. J. Med. vol. 327, pp. 1556-1563 (1992).

Woody et al., "Prolactin exerts hematopoietic growth-promoting effects in vivo and partially counteracts myelosuppression by azidothymidine," Experimental Hematology 27: 811-816 (1999).

Wrighton, N.C. et al., "Small peptides as potent mimetics of the protein hormone erythropoietin," Science, vol. 273, No. 5274, pp. 458-464 (1996).

Wu, H. Y. et al., "Expression of QKI proteins and MAP1B identifies actively myelinating oligodendrocytes in adult rat brain," Mol. Cell. Neurosci., vol. 17, pp. 292-302 (2001).

XP-002582723, NCT00362414 on Aug. 9, 2006: ClinicalTrails.gov Archive.

Yong, VW. "Prospects of repair in multiple sclerosis," Journal of Neurological Sciences. vol. 277, No. Suppl. 1: S16-S18 (2009).

Yuhara, A. et al., "PACAP has a Neurotrophic effect on cultured basal forebrain cholinergic neurons from adult rats," Dev. Brain Res., vol. 131, No. 1, pp. 41-45 (2001).

Zhang et al., "Normal prenatal but arrested postnatal sexual development of luteinizing hormone receptor knockout (LuRKO) mice," Mol. Endocrinol. 15(1): 172-183 (2007).

Zhang et al., "Scent, social status, and reproductive condition in rat like hamsters," J. Physiology & Behavior 74:415-420 (2001).

Figure 10
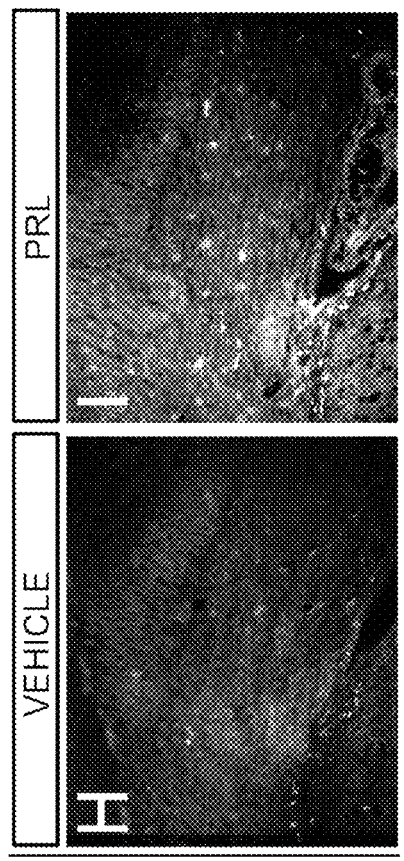
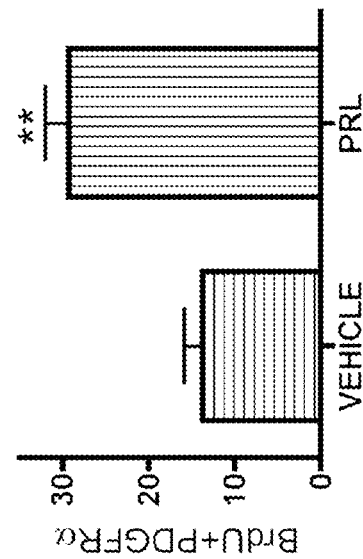

PREGNANCY-INDUCED OLIGODENDROCYTE PRECURSOR CELL PROLIFERATION REGULATED BY PROLACTIN

CROSS-REFERENCE TO RELATED APPLICATIONS

The present application is a divisional of U.S. application Ser. No. 12/419,676, filed Apr. 7, 2009, which is a continuation of U.S. application Ser. No. 11/535,898 (now U.S. Pat. No. 7,534,765), filed Sep. 27, 2006 which claims the benefit of U.S. Provisional Application No. 60/721,025, filed Sep. 27, 2005, and U.S. Provisional Application No. 60/799,280, filed May 9, 2006, all of which are incorporated herein by reference in their entireties.

TECHNICAL FIELD

The present invention relates to the use of compounds for increasing oligodendrocyte production in a mammal.

BACKGROUND

In the adult central nervous system (CNS), specialized cells called oligodendrocytes function to generate myelin sheaths that coat subpopulations of axons, forming the white matter of the brain. The myelin sheath functions to enhance signal conduction by neurons and is required for neuronal health. Defects in myelination or damage to CNS myelin is thought to be central to the impairment of normal brain function in many CNS disorders, including Multiple Sclerosis (Bruck, W. et al *Curr Opin Neurol* 18:221 (2005); Kieseier, B. C. et al *Curr Opin Neurol* 18:211 (2005); Lubetzki, C. et al *Curr Opin Neurol* 18:237 (2005)), spinal cord injury (Keirstead, H. S. et al *J Neurosci* 25:4694 (2005)), age-related dementia (Buckner, R. L. *Neuron* 44:195 (2004); Peters, A. *J Neurocytol* 31:581 (2002)); depression and bipolar disorders (Aston, C. et al *Mol Psychiatry* 10:309 (2005); Bartzokis, G. et al *Neurobiol Aging* 25:843 (2004); Lyoo, I. K. et al *Compr Psychiatry* 43:361 (2002); Moore, P. B. et al *Br J Psychiatry* 178:172 (2001); Silverstone, T. et al *Bipolar Disord* 5:53 (2003)), as well as many of the cognitive impairments following stroke (Inzitari, D. *Stroke* 34:2067 (2003); Jokinen, H. et al *Eur J Neurol* 11:825 (2004); Wardlaw, J. M. et al *Neurology* 59:1381 (2002)).

The adult mammalian CNS contains oligodendrocyte precursor cells (OPCs) throughout both grey and white matter regions, which function to generate new oligodendrocytes throughout adulthood (Gensert, J. M. et al *Glia* 17:39 (1996); Levine, J. M. et al *Trends Neurosci* 24:39 (2001); Levison, S. W. et al *J Neurosci Res* 57:435 (1999); Lubetzki, C. et al *Curr Opin Neurol* 18:237 (2005)). As a result of OPC proliferation the number of oligodendrocytes increases in the adult rodent and primate brain with age (Ling, E. A. et al *J Comp Neurol* 149:73 (1973); Peters, A. *J Neurocytol* 31:581 (2002); Peters, A. et al *Anat Rec* 229:384 (1991)). Further, OPCs are thought to generate new oligodendrocytes in response to injury, which to a limited extent can remyelinate regions of myelin damage (Armstrong, R. C. et al *J Neurosci* 22:8574 (2002); Gensert, J. M. et al *Glia* 17:39 (1996); Stangel, M. et al *Prog Neurobiol* 68:361 (2002)). Presently, little is known about the physiological mechanisms that regulate endogenous OPC proliferation and oligodendrocyte generation in the adult CNS. However, the discovery of these mechanisms may have dramatic implications for the treatment of brain injury and disease through the development of methods to promote the proliferation of OPCs and the generation of new myelinating oligodendrocytes capable of repairing demyelinated CNS tissue (Levine, J. M. et al *Trends Neurosci* 24:39 (2001); Lubetzki, C. et al *Curr Opin Neurol* 18:237 (2005); Stangel, M. et al *Prog Neurobiol* 68:361 (2002)). Consequently, it is desirable to discover signaling molecules capable of promoting OPC proliferation such that these cells may be expanded either in vitro for transplantation or in vivo to promote endogenous white matter repair.

SUMMARY

The present invention relates to methods of producing oligodendrocytes in vivo or in vitro by contacting neural stem cells and/or oligodendrocyte precursor cells with prolactin. We demonstrate herein that prolactin significantly increased the number of oligodendrocytes produced from neural stem cells. This method can be used to enhance myelination, particularly remyelination of a mammal with a demyelinating disease. Therefore, the present invention also provides a method of treating or ameliorating a demyelinating disease or condition and/or a disease or condition associated with demyelination by using prolactin.

Accordingly, in one aspect, the invention provides a method of delivering oligodendrocytes to a mammal, comprising:

(a) introducing at least one neural stem cell and/or oligodendrocyte precursor cell into said mammal; and (b) administering an effective amount of a prolactin or a prolactin inducing agent to said mammal; under conditions that result in oligodendrocyte formation from said neural stem cell and/or oligodendrocyte precursor cell.

The invention also provides a method of delivering oligodendrocytes to a mammal, comprising administering to said mammal an effective amount of a pharmaceutical composition comprising:

(a) at least one neural stem cell and/or oligodendrocyte precursor cell; and (b) an effective amount of a prolactin or a prolactin inducing agent to said mammal;

under conditions that result in oligodendrocyte formation from said neural stem cell and/or oligodendrocyte precursor cell.

The method may further include contacting said neural stem cells and/or oligodendrocyte precursor cells with at least one biological agent that is capable of increasing the number of said neural stem cell and/or oligodendrocyte precursor cells. The biological agent may be used before, after, or both before and after said introduction of said neural stem cell and/or oligodendrocyte precursor cell into said mammal.

The biological agent may be selected from the group consisting of epidermal growth factor (EGF), pituitary adenylate cyclase-activating polypeptide (PACAP), fibroblast growth factor (FGF), transforming growth factor alpha (TGFα), ciliary neurotrophic factor (CNTF), Leukemia Inhibitory Factor (LIF), platelet-derived growth factor (PDGF), estrogen, ovarian hormone, human chorionic gonadotrophin (hCG), growth factor and insulin-like growth factor-1.

The mammal may be, for example, a human, canine, feline, rodent, sheep, goat, cattle, horse, pig, or non-human primate. The mammal is preferably a human.

The neural stem cells may be obtained from the subventricular zone in the forebrain of said mammal and oligodendrocyte precursor cells are obtained from any location in the central nervous system of said mammal, for example the optic nerve, corpus callosum, and/or spinal cord. The mammal may be an embryonic mammal, a neonatal mammal, or an adult mammal.

The method may further comprise applying an effective amount of a factor that promotes oligodendrocyte differentiation, growth, proliferation or survival, for example triiodothyronine.

In another aspect, the invention provides a method for treating or ameliorating a disease or condition associated with demyelination in a mammal comprising:
(a) culturing mammalian neural stem cell and/or oligodendrocyte precursor cells;
(b) transplanting said neural stem cell and/or oligodendrocyte precursor cells into a mammal; and
(c) administering a proliferation agent to said mammal in order to induce said neural stem cells and/or oligodendrocyte precursor cells to generate oligodendrocytes.

The proliferation agent is, for example, prolactin. The mammalian neural stem cell and/or oligodendrocyte precursor cell culture may be prepared using mammalian brain tissue selected from the group consisting of embryonic brain tissue, neonatal brain tissue, and adult brain tissue. The neural stem cells are preferably obtained from the subventricular zone in the forebrain of said mammal and the oligodendrocyte precursor cells may be obtained from any location in the central nervous system of said mammal, for example the optic nerve, corpus callosum, and/or spinal cord. In one embodiment, the neural stem cells and/or oligodendrocyte precursor cells are harvested from said mammal for autologous transplantation.

The method may further comprise the step of applying an effective amount of a factor that promotes oligodendrocyte differentiation, growth, proliferation or survival such as tri-iodothyronine.

The prolactin may be administered intrathecally, intravascularly, intravenously, intramuscularly, intraperitoneally, transdermally, intradermally, subcutaneously, orally, topically, rectally, vaginally, nasally, or by inhalation. The prolactin is preferably administered by injection or infusion.

The neural stem cell and/or oligodendrocyte precursor cells may be expanded in vivo, by administering to said mammal a biological agent that is known to increase the number of neural stem cell and/or oligodendrocyte precursor cells. The biological agent may be selected from the group consisting of epidermal growth factor (EGF), pituitary adenylate cyclase-activating polypeptide (PACAP), fibroblast growth factor (FGF), transforming growth factor alpha (TGFα), ciliary neurotrophic factor (CNTF), leukemia Inhibitory Factor (LIF), platelet-derived growth factor (PDGF), estrogen, ovarian hormone, human chorionic gonadotrophin (hCG), growth factor and insulin-like growth factor-1.

The neural stem cells and/or oligodendrocyte precursor cells may be introduced into the brain, optic nerve or spinal cord of said mammal. In one embodiment, they may be introduced into a site where axons have been demyelinated.

The disease or condition associated with demyelination may include, for example, multiple sclerosis, acute disseminated encephalomyelitis, diffuse cerebral sclerosis, necrotizing hemorrhagic encephalitis, leukodystrophies, stroke, spinal cord injury, schizophrenia, bipolar disorder, acute brain injury, and dementia. In one embodiment, the disease or condition is multiple sclerosis.

In yet another aspect, the invention provides a method for enhancing the formation of oligodendrocytes endogenously in a mammal, comprising administering an effective amount of a prolactin to said mammal. In one embodiment, the mammal is suffering from or suspected of having a disease or condition associated with demyelination. The disease or condition associated with demyelination may be selected from the group consisting of multiple sclerosis, acute disseminated encephalomyelitis, diffuse cerebral sclerosis, necrotizing hemorrhagic encephalitis, leukodystrophies, stroke, spinal cord injury, schizophrenia, bipolar disorder, acute brain injury, and dementia. In one embodiment, the disease or condition is multiple sclerosis.

The method may further comprise administration of at least one biological agent that is capable of increasing the number of neural stem cells and/or oligodendrocyte precursor cells in said mammal. The biological agent may be epidermal growth factor (EGF), pituitary adenylate cyclase-activating polypeptide (PACAP), fibroblast growth factor (FGF), transforming growth factor alpha (TGFα), ciliary neurotrophic factor (CNTF), Leukemia Inhibitory Factor (LIF), platelet-derived growth factor (PDGF), estrogen, ovarian hormone, human chorionic gonadotrophin (hCG), growth factor or insulin-like growth factor-1.

The prolactin may be administered systemically, subcutaneously, or into the brain.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10 shows an increase in oligodendrocyte precursor cell proliferation in the corpus collosum of mice following three days of prolactin (PRL) administration compared to the control (vehicle) mice;

Like reference symbols in the various drawings indicate like elements.

DETAILED DESCRIPTION

Figure 1:
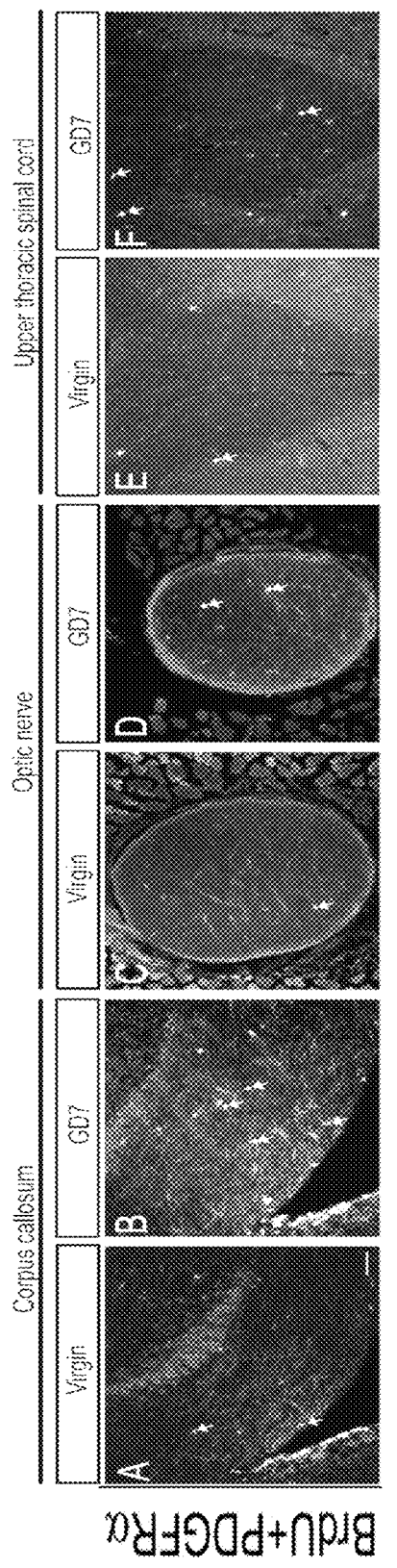
FIG. 1 shows double staining in the corpus collosum, the optic nerve and spinal cord using the oligodendrocyte precursor specific immuno-marker PDGFRα with BrdU in gestational day 7 pregnant (GD7) and non-pregnant (virgin) mice.

The present invention provides a method of increasing OPC proliferation in vitro and in vivo by using the hormone prolactin. Prolactin can be applied in combination with a biological agent capable of increasing the number of neural stem cells and/or OPCs (e.g., platelet-derived growth factor (PDGF)) to enhance adult OPC proliferation in vitro. Other biological agents which can be used in combination with prolactin include, but are not limited to, epidermal growth factor (EGF), pituitary adenylate cyclase-activating polypeptide (PACAP), fibroblast growth factor (FGF), transforming growth factor alpha (TGFα), ciliary neurotrophic factor (CNTF), leukemia inhibitory factor (LIF), estrogen, ovarian hormone, human chorionic gonadotrophin (hCG), growth factor, and insulin-like growth factor-1. The cultured OPCs can be used, for example, for transplantation to treat demyelinated lesions. Alternatively, prolactin can be delivered in vivo subcutaneously to promote OPC proliferation in situ within the adult forebrain and spinal cord to potentially promote endogenous remyelination of demyelinated CNS white matter.

Pregnancy has previously been reported to promote neural stem cell proliferation in the maternal forebrain subventricular zone (Shingo, T. et al *Science* 299:117 (2003)). In addition to adult neural stem cells, OPCs are known to reside throughout the adult CNS, including but not limited to, the optic nerve, corpus callosum, and spinal cord. OPCs can be recognized in vivo by their expression of the PDGFRalpha and the proteoglycan NG2 (Stangel, M. et al *Prog Neurobiol* 68:361 (2002)). Cellular proliferation can be identified by the incorporation of the thymidine analog bromodeoxyuridine (BrdU) during S-phase of the cell cycle, which in combination with OPC specific staining can identify OPC proliferation.

Definitions

A "multipotent neural stem cell", or "neural stem cell", is a stem cell in the neural cell lineage. A stem cell is a cell which is capable of reproducing itself. In other words, when a stem cell divides, at least some of the resulting daughter cells are also stem cells. Neural stem cells and their progeny are capable of differentiating into all the cell types in the neural cell lineage, including neurons, astrocytes and oligodendrocytes (astrocytes and oligodendrocytes are collectively called glia or glial cells). Therefore, the neural stem cells are multipotent neural stem cells. Multipotent neural stem cells are described, for example, in U.S. Pat. Nos. 5,750,376 and 5,851,832.

The adult neural stem cells preferably refer to the neural stem cells located in or derived from the subventricular zone (SVZ) of the forebrain of adult mammals, which are different from the proliferating cells in the adult hippocampus.

The "progeny" of neural stem cells described herein refers to any and all cells derived from neural stem cells as a result of proliferation or differentiation.

An "oligodendrocyte precursor cell" is a central nervous system precursor cell capable of giving rise to oligodendrocytes.

A "mammal" is any member in the mammalian family. A mammal is preferably a primate, rodent, feline, canine, domestic livestock (such as cattle, sheep, goats, horses, and pigs), and most preferably a human.

A "demyelinating disease" is a disease or medical condition that is caused by or associated with demyelination. Examples of these diseases or conditions include multiple sclerosis (including the relapsing and chronic progressive forms of multiple sclerosis, acute multiple sclerosis, neuromyelitis optica (Devic's disease)), diffuse cerebral sclerosis (including Shilder's encephalitis periaxialis diffusa and Balo's concentric sclerosis). Demyelinating disease also include a variety of diseases wherein demyelination is caused by viral infections, vaccines and genetic disorders. Examples of these demyelinating diseases include acute disseminated encephalomyelitis (occurring after measles, chickenpox, rubella, influenza or mumps; or after rabies or smallpox vaccination), necrotizing hemorrhagic encephalitis (including hemorrhagic leukoencephalitis), and leukodystrophies (including Krabbe's globoid leukodystrophy, metachromatic leukodystrophy, adrenoleukodystrophy, Canavan's disease and Alexander's disease). The demyelinating disease is preferably multiple sclerosis or diffuse cerebral sclerosis, and most preferably sclerosis.

"Treating or ameliorating" means the reduction or complete removal of the symptoms of a disease or medical condition.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

"Prolactin" is a polypeptide which (1) shares substantial sequence similarity with a native mammalian prolactin, preferably the native human prolactin; and (2) possesses a biological activity of the native mammalian prolactin. The native human prolactin is a 199-amino-acid polypeptide synthesized mainly in the pituitary gland. Thus, the term "prolactin" encompasses prolactin analogs which are the deletional, insertional, or substitutional mutants of the native prolactin. Furthermore, the term "prolactin" encompasses the prolactins from other species and the naturally occurring variants thereof.

In addition, a "prolactin" may also be a functional agonist of a native mammalian prolactin receptor. For example, the functional agonist may be an activating amino acid sequence disclosed in U.S. Pat. No. 6,333,031 for the prolactin receptor; a metal complexed receptor ligand with agonist activities, for the prolactin receptor (U.S. Pat. No. 6,413,952); G120RhGH which is an analog of human growth hormone but acts as a prolactin agonist (Mode, et al *Endocrinology* 137:447(1996)); or a ligand for the prolactin receptor as described in U.S. Pat. Nos. 5,506,107 and 5,837,460.

Specifically included as a member of the prolactin family are the naturally occurring prolactin variants, prolactin-related protein, placental lactogens, S179D-human prolactin (Bernichtein, S. et al. *Endocrin* 142:2950 (2001)), prolactins from various mammalian species, including but not limited to, human, other primates, rat, mouse, sheep, pig, cattle, and the prolactin mutants described in U.S. Pat. Nos. 6,429,186 and 5,995,346.

A "prolactin inducing agent" is a substance that, when given to an animal, is capable of increasing the amount of prolactin in the mammal. For example, prolactin releasing peptide stimulates the secretion of prolactin.

To "transplant" a composition into a mammal refers to introducing the composition into the body of the mammal by any method established in the art. The composition being introduced is the transplant, and the mammal is the "recipient". The transplant and the recipient may be syngenic, allogenic or xenogenic. Preferably, the transplantation is an autologous transplantation.

Methods

Methods for the isolation and in vitro culture of multipotent neural stem cells have recently been developed (for example, see U.S. Pat. Nos. 5,750,376; 5,980,885; 5,851,832). It was discovered that fetal brains can be used to isolate and culture multipotent neural stem cells in vitro. These stem cells, either from fetal or adult brains, are capable of self-replicating. The progeny cells can again proliferate or differentiate into any cell in the neural cell lineage, including neurons, astrocytes and oligodendrocytes.

Most of the cells differentiated from neural stem cells are astrocytes. Therefore, although neural stem cells provide a good source of all kinds of mature or immature neural cells, using neural stem cells to produce oligodendrocytes for demyelinating diseases is normally an inefficient process. The present invention, however, provides a method of significantly increasing the efficiency of oligodendrocyte production from neural stem cells. The addition of prolactin to a neural stem cell culture induces their differentiation preferentially into oligodendrocytes. Prolactin also increases oligodendrocyte production from OPCs.

The oligodendrocytes produced from the neural stem cell or OPC culture can be introduced (e.g., by transplantation) into a mammal, particularly to compensate for lost or dysfunctional oligodendrocytes. The mammal is preferably a human, canine, feline, rodent, sheep, goat, cattle, horse, pig, or non-human primate. Most preferably, the mammal is human. Since neural stem cells can be cultured from brain tissues from mammals of any age including adults, it is preferable to grow neural stem cells using a mammal's own tissue for autologous transplantation. Allogenic and xenogenic transplantations are also possible, particularly when the transplantation site is in the brain, where immunologic rejection is less severe due to the blood-brain barrier.

It is also contemplated that neural stem cells can be transplanted into a mammal and induced to form oligodendrocytes in vivo. Thus, neural stem cells may be expected in culture using established methods, transplanted into the mammal, and contacted in vivo with the oligodendrocyte promoting factor to produce oligodendrocytes. Optionally, the transplanted neural stem cells can be expanded again in vivo by administering to the mammal a biological agent that is known to increase the number of neural stem cells as disclosed above.

The cells are preferably introduced into the brain or spinal cord of the mammal, particularly at sites where oligodendrocytes are insufficient, for example, around axons that have been demyelinated. In humans, areas of demyelination are generally associated with plaque like structures, which can be visualized with magnetic resonance imaging (MRI). The cells may also be transplanted into other areas of the central nervous system, as glial cells are known to be able to migrate to their neural targets. A particularly useful approach is to transplant into the "mirror image" location of a target lesion in the other hemisphere, since cells are known to efficiently migrate to the corresponding location in the opposite hemisphere through the corpus collosum (Learish, R. D. et al *Ann Neurol* 46:716 (1999)).

The prolactin can be administered by any suitable route established in the art, including for example, intrathecally, intravascularly, intravenously, intramuscularly, intraperitoneally, transdermally, intradermally, subcutaneously, orally, topically, rectally, vaginally, nasally or by inhalation. The preferred method of administration is by injection (e.g., with a needle or catheter) or infusion.

The present invention further provides a method of enhancing oligodendrocyte production in vivo by administering the oligodendrocyte promoting factor to a mammal under conditions that result in oligodendrocyte formation. The resultant oligodendrocytes are capable of remyelinating demyelinated neurons in the mammal, whereby diseases or conditions in the mammal that are associated with demyelination can be treated or ameliorated.

It is contemplated that the present invention can be used to prevent demyelinating disease where a mammal is at risk of such diseases. Although the causes of multiple sclerosis are not entirely clear, certain risk factors have been identified. For example, multiple sclerosis (MS) occurs in 1-2% of first-degree relatives of MS patients, and people with certain histocompatibility antigens are correlated with MS as well. Therefore, the present invention may be used to prevent MS in the high-risk group.

The following examples are offered to illustrate this invention and are not to be construed in any way as limiting the scope of the present invention.

EXAMPLE 1

Pregnancy Promotes OPC Proliferation

Six to eight week old virgin or gestational day 7 (GD7) pregnant female CD-1 mice received 6 injections of BrdU (120 mg/kg, i.p., dissolved in 0.007% NaOH in phosphate buffer), each 2 hours apart, and were sacrificed 30 minutes following the last injection. Animals were transcardially perfused with 4% paraformaldehyde, cryoprotected with 25% sucrose, and the brains, spinal cords and optic nerves were embedded in OCT compound. Tissue was cryosectioned at 14 microns in a 1 in 7 series with 12 sections per slide and processed for immunohistochemistry. Antibodies used included rat anti-BrdU (Seralab), guinea pig anti-NG2 (gift from Dr. William Stallcup; Burnham Institute; La Jolla, Calif.), goat anti-PDGFRalpha (R&D). Primary antibodies were recognized with the appropriate secondary FITC and CY3 conjugated secondary antibodies (Jackson ImmunoResearch). Antibodies were diluted in 10% normal donkey serum and 0.03% triton-X in phosphate buffered saline. For BrdU staining, tissues were treated with 1M HCl for 30 min at 60 degrees C. to denature cellular DNA.

Quantification of the number of dividing cells (BrdU+ cells), OPC (PDGFRalpha+ and NG2+ cells), and dividing OPCs (BrdU+PDGFRalpha or BrdU+NG2 double positive cells) revealed a significant increase in each of these cell populations within the corpus callosum, spinal cord, and optic nerve of GD7 pregnant females relative to virgin controls (Table 1). These findings reveal the novel finding that pregnancy triggers increased proliferation of OPCs throughout the maternal CNS.

Figure 4:
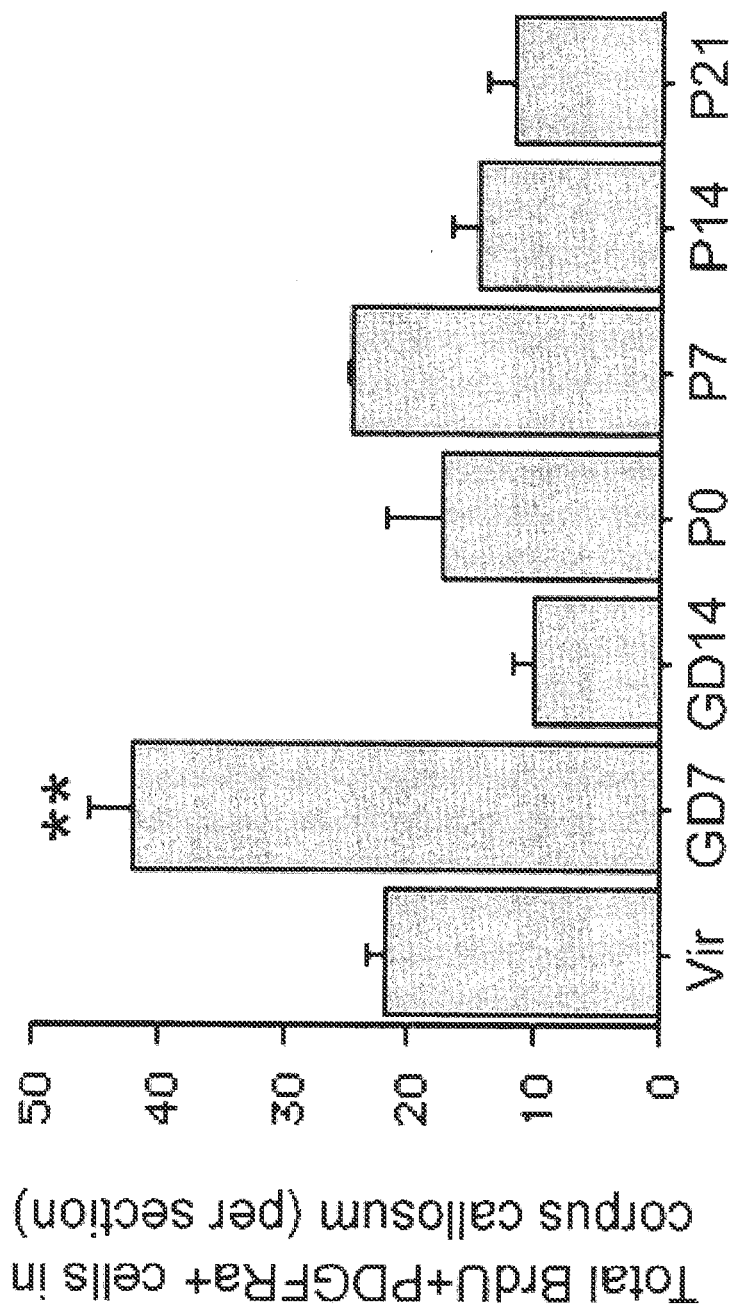
FIG. 4 shows a time course of oligodendrocyte precursor cell proliferation, determined through quantification of BrdU immunoreactivity by PDGFRalpha expressing cells in the corpus collosum over the course of pregnancy (GD7, GD14) and the postpartum period (P0, P7, P14, P21)
Figure 5:
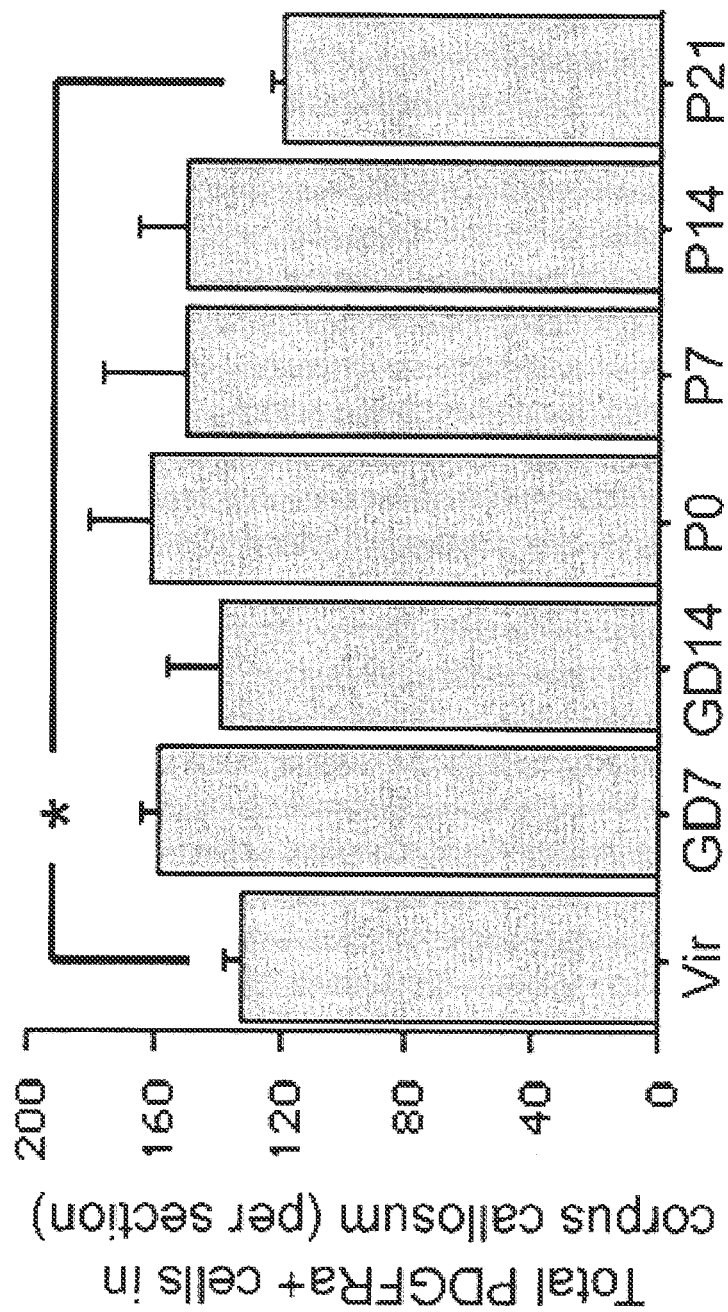
FIG. 5 shows a time course of total oligodendrocyte precursor cell number, determined by total number of PDGFRalpha expressing cells in the corpus collosum over the course of pregnancy (GD7, GD14) and the postpartum period (P0, P7, P14, P21.

A time course analysis of OPC proliferation and numbers over the course of pregnancy and during the postpartum period revealed that OPC proliferation and numbers peak during the first week of pregnancy (GD7) and return to control levels during the postpartum period (FIGS. 4 and 5).

EXAMPLE 2

Pregnancy Promotes Generation of New Mature Oligodendrocytes

To trace the generation of new mature oligodendrocytes 6 injections of BrdU were given on GD7 of pregnancy and the animals were allowed to survive for 11 days to GD18 to permit the newly generated OPCs to differentiate into mature oligodendrocytes. Virgin females were used as controls. Mature oligodendrocytes were identified by expression of the mature oligodendrocyte marker GSTpi using mouse anti-GSTpi antibodies.

TABLE 1

| Region/Marker | Virgin | GD7 | |
|---|---|---|---|
| Corpus callosum | | | |
| BrdU | 32 ± 5.1 | **57 ± 2.3 | ($p < 0.01$; n = 3) |
| BrdU + PDGFRα | 22 ± 1.4 | **42 ± 3.5 | ($p < 0.01$; n = 3) |
| PDGFRα | 130 ± 5.3 | *158 ± 6.4 | ($p < 0.01$; n = 7) |
| NG2 | 92 ± 5.9 | *204 ± 26 | ($p < 0.05$; n = 3) |
| GD7-18 trace BrdU + GSTpi | 8.6 ± 0.9 | **15 ± 1.2 | ($p < 0.01$; n = 3) |
| Optic nerve | | | |
| BrdU | 1.2 ± 0.3 | *2.2 ± 0.6 | ($p < 0.05$; n = 4) |
| BrdU + PDGFRα | 0.83 ± 0.3 | **3.0 ± 0.2 | ($p < 0.01$; n = 4) |
| PDGFRα | 16 ± 2 | *22 ± 0.7 | ($p < 0.05$; n = 4) |
| NG2 | 11 ± 0.8 | **16 ± 1.3 | ($p < 0.01$; n = 4) |
| GD7-18 trace BrdU + GSTpi | 0.19 ± 0.05 | *0.46 ± 0.07 | ($p < 0.05$; n = 4) |
| Spinal cord | | | |
| BrdU | 5.8 ± 1.0 | *14 ± 3.1 | ($p < 0.05$; n = 5) |
| BrdU + PDGFRα | 2.3 ± 0.5 | *8.4 ± 2 | ($p < 0.05$; n = 5) |
| PDGFRα | 92 ± 25 | *166 ± 24 | ($p < 0.05$; n = 5) |
| NG2 | 124 ± 11 | *310 ± 33 | ($p < 0.05$; n = 3) |
| BrdU + NG2 | 2.5 ± 0.4 | **6.7 ± 0.7 | ($p < 0.01$; n = 3) |
| GD7-18 trace BrdU + GSTpi | 1.5 ± 0.01 | *4.1 ± 0.7 | ($p < 0.05$; n = 5) |

Figure 6:
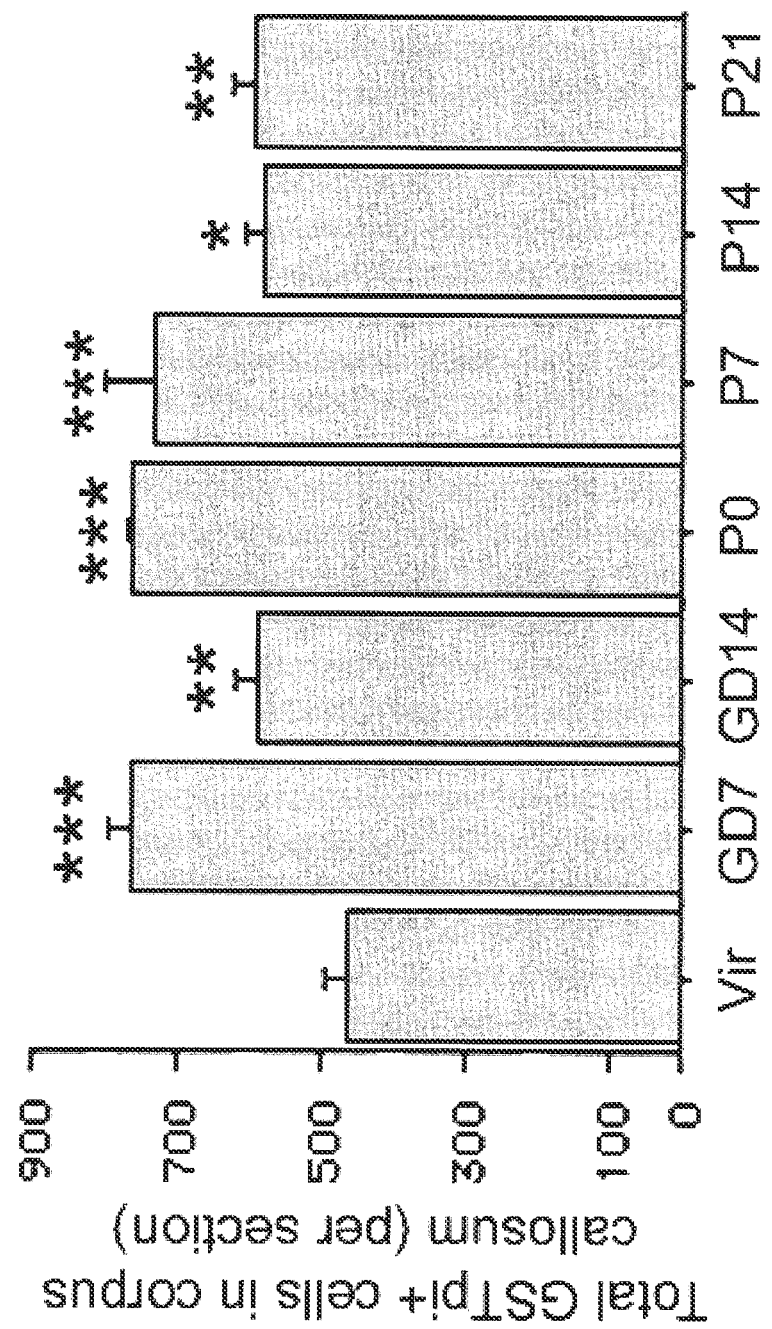
FIG. 6 shows a time course of mature oligodendrocyte cells, determined by total number of GSTpi expressing cells in the corpus collosum over the course of pregnancy (GD7, GD14) and the postpartum period (P0, P7, P14, P21.

As shown in Table 1, animals that received the trace BrdU injections on GD7 of pregnancy had approximately double the number of newly born, mature oligodendroctyes (BrdU+ GSTpi double positive cells) within the corpus callosum, spinal cord, and optic nerve 11 days later relative to virgin controls. Therefore, the increase in OPC proliferation led to an increase in the generation of new oligodendrocytes in the maternal CNS. Additionally, the total number of mature oligodendrocytes (GSTpi+ cells) in the corpus callosum of during pregnancy and the postpartum period was examined (FIG. 6). The results demonstrate that pregnancy triggers a significant increase in the total number of mature oligodendrocytes relative to virgin controls that persists up to three weeks postpartum.

Statistical analysis was performed using the unpaired t-test or an ANOVA followed by the Tukey Honest Significant Difference post-hoc test.

EXAMPLE 3

Figure 2:
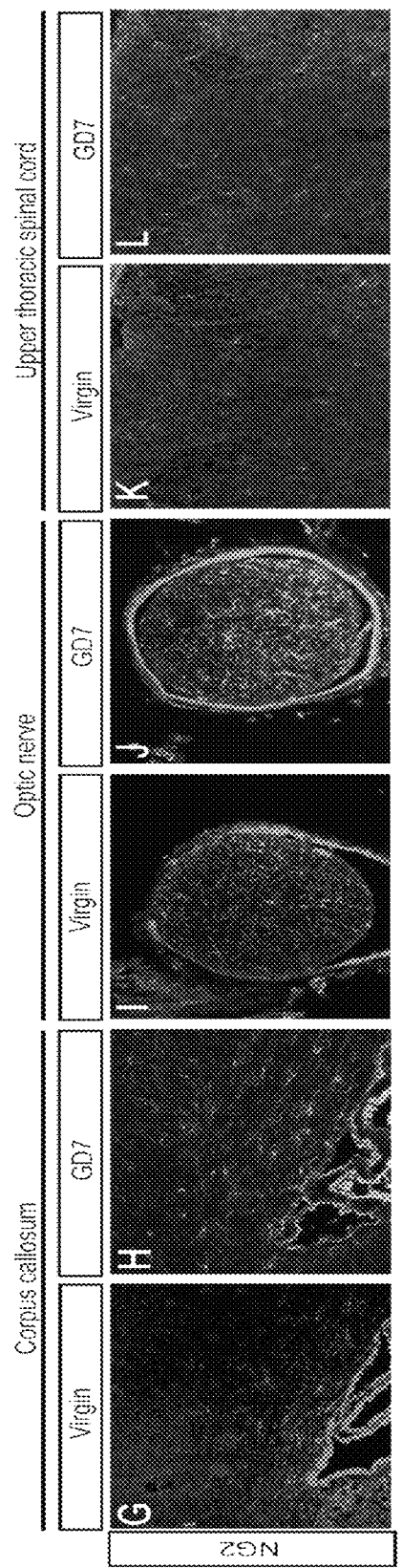
FIG. 2 shows double staining in the corpus collosum, the optic nerve and spinal cord using the oligodendrocyte precursor specific immuno-marker NG2 with BrdU in gestational day 7 pregnant (GD7) and non-pregnant (virgin) mice.

Pregnancy Promotes Oligodendrocyte Precursor Cell Proliferation Throughout the Maternal Central Nervous System Increased numbers of BrdU+ cells were observed in the corpus callosum, spinal cord, and optic nerve of the GD7 pregnant maternal CNS (Table 1); as well, significantly increased numbers of PDGFRalpha+ cells (FIG. 1, Table 1) and NG2+ (FIG. 2, Table 1) OPCs were observed in the pregnant animals. An increase in the total number of dividing OPCs was observed in each of these tissues at GD7 as indicated by an increase in the number of BrdU+PDGFRalpha double positive cells (FIG. 1, Table 1).

Figure 3:
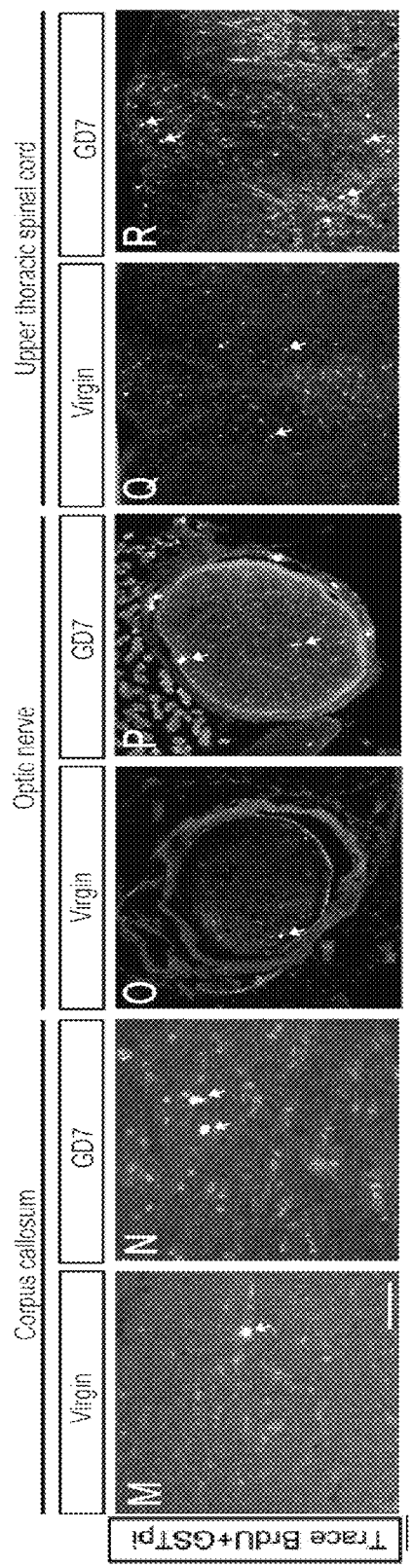
FIG. 3 shows double staining in the corpus collosum, the optic nerve and spinal cord using the mature oligodendrocyte specific immuno-marker GSTpi with BrdU in gestational day 7 pregnant (GD7) and non-pregnant (virgin) mice.

BrdU was given to GD7 or virgin mice and traced for 11 days and revealed an increase in the number of BrdU+GSTpi double positive cells in the corpus callosum, optic nerve, and spinal cord in the pregnant (GD7) versus non-pregnant (virgin) mice (FIG. 3, Table 1). Therefore, the induction of OPC proliferation in response to pregnancy results in an increased generation of new mature oligodendrocytes throughout the maternal CNS.

A time course of OPC proliferation in the corpus callosum during pregnancy and the postpartum period (FIG. 4) revealed a peak of BrdU+PDGFRalpha expressing cells at GD7, which dropped below virgin levels at GD14, but returned to virgin levels by term and was maintained at these levels during the postpartum period.

An examination of changes in the total number of OPCs in the corpus callosum during pregnancy (FIG. 5) revealed a significant increase in the number of PDGFRalpha expressing cells at GD7, which dropped back to baseline levels by 21 days postpartum.

Figure 7:
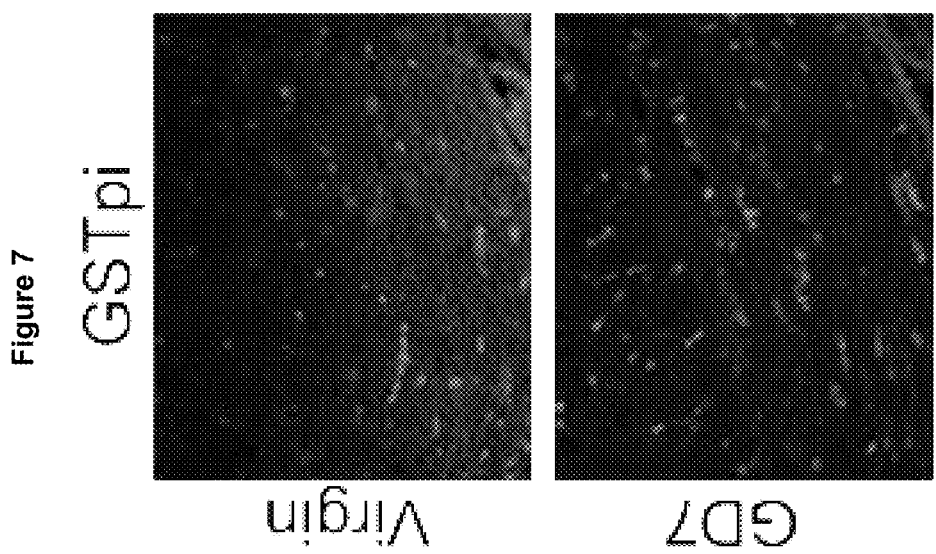
FIG. 7 shows the increased presence of mature oligodendrocyte cells via GSTpi immunostaining, in the corpus collosum of pregnant (GD7) compared to non-pregnant (virgin) mice.

An examination of changes in the total number of mature oligodendrocytes in the corpus callosum during pregnancy (FIG. 6) revealed that pregnancy results in a significant increase in oligodendrocyte number by GD7 and this increase remains significantly higher than virgin levels throughout pregnancy and up to 21 days postpartum. FIG. 7 shows the changes in mature oligodendrocytes in the corpus callosum during pregnancy as evidenced by GSTpi staining.

EXAMPLE 4

Prolactin Regulates Pregnancy Induced OPC Proliferation

Figure 8:
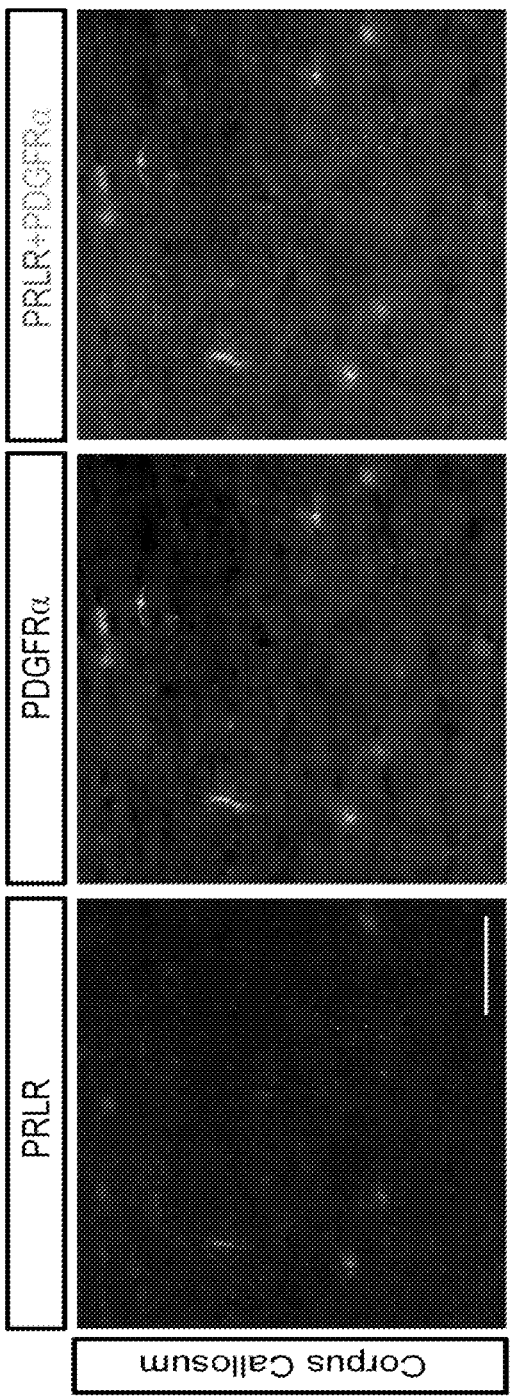
FIG. 8 shows the co-localization of the prolactin receptor (PRLR) and the oligodendrocyte precursor cell specific marker PDGFRalpha in the corpus collosum.

To investigate whether adult OPCs express the prolactin receptor, 6-8 week old adult female virgin CD-1 mice were transcardially perfused with 4% paraformaldehyde, cryoprotected in 25% sucrose and processed for cryosectioning at 14 microns as described previously. Immunohistochemistry was performed as described above using mouse anti-prolactin receptor (PRLR, Affinity Bioreagents Inc.) and goat anti-PDGFRalpha. The corpus callosum was examined for the presence of double-labeled cells. Double labeling revealed the presence of PDGFRalpha expressing OPCs that also expressed the prolactin receptor. As the prolactin receptor is expressed by a subpopulation of PDGFRalpha positive OPCs (FIG. 8), these results suggested that prolactin potentially regulates OPC proliferation

EXAMPLE 5

Prolactin is Required for Induction of OPC Proliferation

To investigate whether prolactin signaling was required for the induction of OPC proliferation within the maternal forebrain during pregnancy prolactin receptor mutant heterozygous mice (PRLR +/−), relative to wildtype controls (PRLR +/+), were analyzed. Animals were genotyped using PCR according to previously published methods (Shingo, T. et al *Science* 299:117 (2003)). Non-pregnant (virgin) versus pregnant (GD7) PRLR +/+ and +/− females received BrdU injections as described above and were sacrificed 30 minutes following the final BrdU injection. Immunohistochemical analysis for BrdU and PDGFRalpha was performed and the number of double positive cells in the corpus callosum was quantified (as described above).

Figure 9:
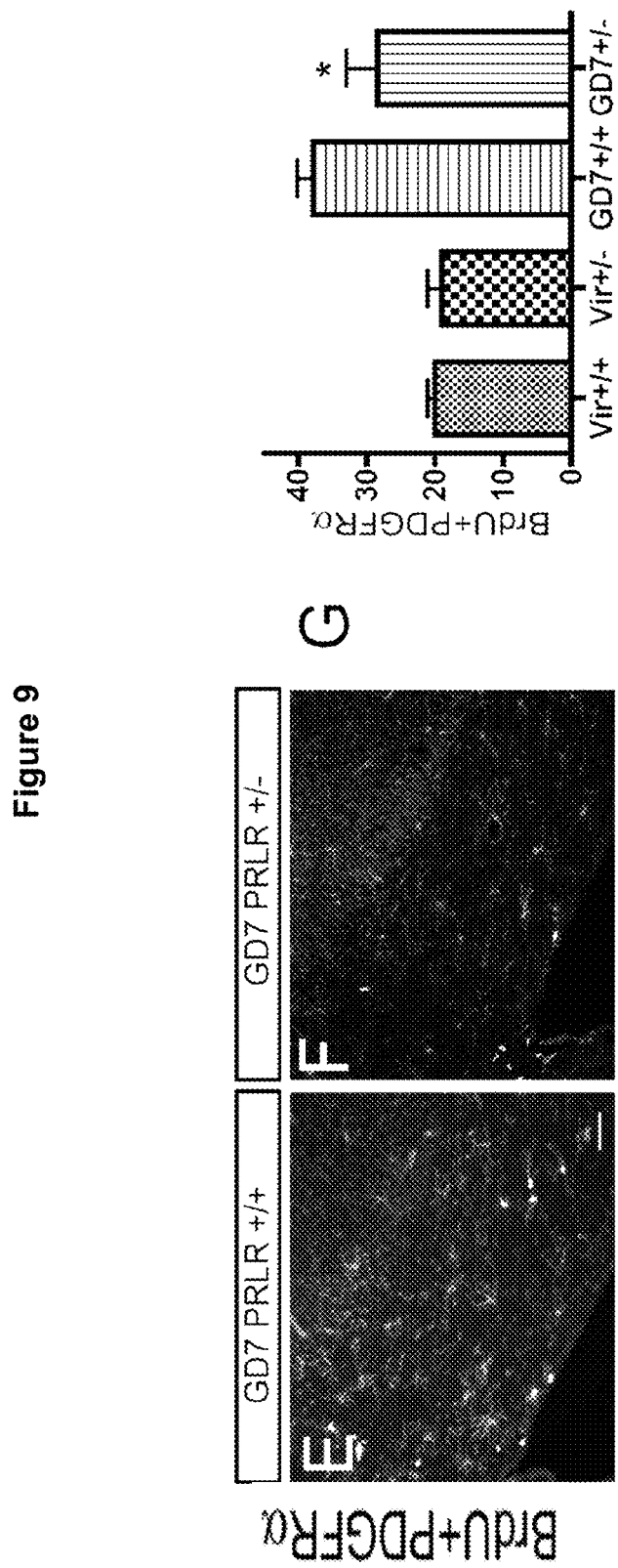
FIG. 9 shows decreased proliferation of oligodendrocyte precursor cells in the corpus collosum of mutant mice heterozygous for the prolactin receptor (+/−) as compared to normal mice (+/+) exposed to prolactin.

Decreased prolactin receptor signaling in the PRLR +/− animals resulted in a significant decrease in pregnancy-induced OPC proliferation in the corpus callosum (FIG. 9). PRLR +/− mice experience a significant reduction in the number of BrdU+PDGFRalpha expressing cells within the corpus callosum at GD7 relative to wildtype controls (*$p<0.05$; Bonferroni posthoc test; n=4). These results reveal that prolactin signaling is required for the induction of OPC proliferation in response to pregnancy.

To investigate whether prolactin signaling was sufficient to promote the proliferation of OPCs within the maternal forebrain, 6-8 week old virgin CD-1 mice were treated with a 3 day subcutaneous infusion of prolactin (16 micrograms/day; mouse recombinant, National Hormone & Peptide Program, Torrance, Calif.) or vehicle control. Prolactin was dissolved in 0.9% saline containing 1 mg/ml mouse serum albumin (Sigma). Mice received BrdU on the 3rd day of infusion and were sacrificed 30 minutes following the final BrdU injection. Immunohistochemical analysis was performed to determine the number of BrdU+PDGFRalpha double positive cells within the corpus callosum and spinal cord (as described above).

The subcutaneous infusion of prolactin was sufficient to significantly increase OPC proliferation in both the corpus callosum and spinal cord relative to vehicle control infused virgin females (FIG. 10). Three day subcutaneous infusion of prolactin significantly increased the number of BrdU+PDGFRalpha cells within the corpus callosum of virgin female mice relative to vehicle control infusions ($p<0.01$; unpaired t-test, n=4). PRL infusions also increased the number of BrdU+PDGFRalpha positive cells in the spinal cord relative to vehicle control (PRL=11±1; VEH=7±0.9; n=4; $P<0.05$; unpaired t-test). These results demonstrate that prolactin is sufficient to increase OPC proliferation in vivo throughout the CNS.

To investigate whether prolactin was sufficient to increase production of new mature oligodendrocytes, 6-8 week old received 3 day infusions of prolactin or vehicle (as described previously). On the 3rd day of the infusion the animals received 6 BrdU injections (1 every 2 hours) and were left to survive for 12 more days to trace the generation of new mature oligodendrocytes in the corpus callosum. Animals were sacrificed 12 days after the BrdU injections and the number of BrdU+GSTpi expressing cells in the corpus callosum was quantified. Prolactin infused animals had a 36% increase in the number of newly generated oligodendrocytes in the corpus callosum compared to vehicle control infused animals (Table 2). This result reveals that prolactin is sufficient to increase the generation of new mature oligodendrocytes in the adult CNS.

TABLE 2

Number of BrdU + GSTpi co-expressing cells in the corpus callosum

|  | Average Brdu + Gstpi Co-Expressing Cells Per Section |
|---|---|
| Vehicle | 2.9 +/− 0.3 |
| Prolactin | 4.5 +/− 0.2 | n = 5; p = 0.0016; two-tailed unpaired t-test

EXAMPLE 6

Oligodendrocytes Generated by Prolactin Elaborate Processes

Figure 11:
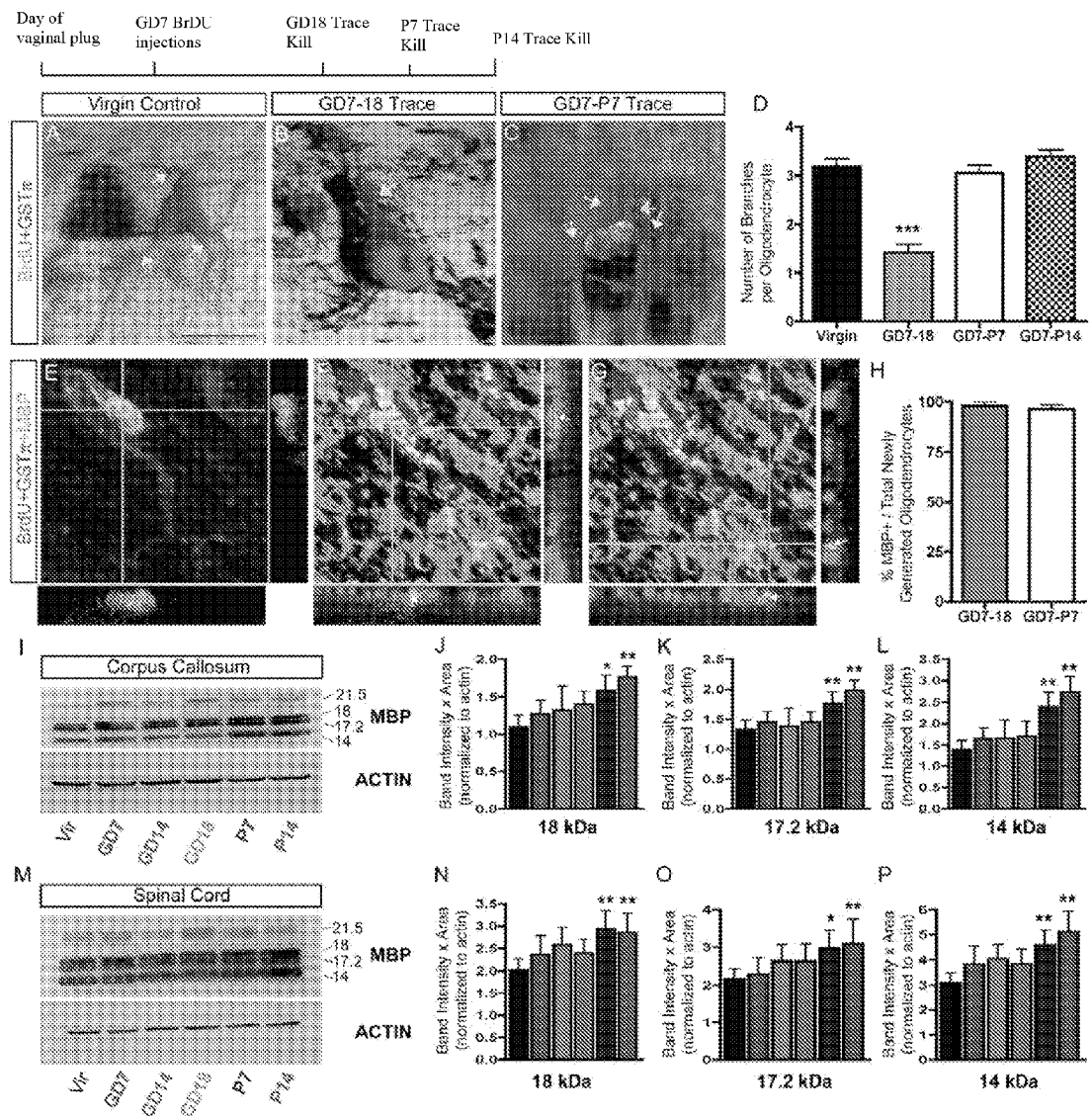
FIG. 11 shows that the newly proliferated oligodendrocytes mature and form processes during late pregnancy and the post-partum period and that oligodendrocytes newly formed during pregnancy generate myelin and increase the overall level of myelination in the corpus collosum.

In order for the newly generated oligodendrocytes to myelinate, they must first form glial processes. GSTpi+ oligodendrocytes in the corpus collosum of virgin females were randomly imaged with confocal z-stacks, which revealed that mature oligodendrocytes extend an average 3-4, highly branched, GSTpi+ processes from the cell soma (FIGS. 11A and D; n=3, Ns25 cells/animal). GD7-18 BrdU tracing was used to identify newly generated oligodendrocytes (BrdU+GSTpi+ cells) in the CC of pregnant females. GD7-18 newly generated oligodendrocytes extended significantly fewer GSTpi+ processes than mature virgin oligodendrocytes, with an average of 1-2 per cell soma (FIG. 11B and D; $p<0.001$; one way ANOVA with Tukey HSD posthoc test; n=3; N≧25 cells/animal), suggesting these cells were still maturing at the end of pregnancy. Indeed, longer tracing times of GD7-P7 and GD7-P14 revealed that the newly generated cells did eventually develop the fully mature average of 3-4 GSTpi− processes per soma during the postpartum period (FIG. 11C and D; n=3; N≧25 cells/animal).

EXAMPLE 7

Oligodendrocytes Induced by Prolactin Increase Overall Myelination

After determining that the newly formed oligodendrocytes form processes, we confirmed that the oligodendrocytes produce myelin. Confocal imaging of cells triple labeled with BrdU, GSTpi, and myelin basic protein (MBP), the major protein constituent of myelin, revealed that virtually all of the newly generated BrdU+GSTpi+ oligodendrocytes in the corpus collosum of GD7-18 animals (~98%; n=3; N≧25 cells/animal) and GD7-P7 animals (~96%; n=3; N≧25 cells/animal), expressed MBP (FIG. 11E-G). Therefore, the new oligodendrocytes appear to generate myelin.

An increase in the number of myelinating oligodendrocytes in the maternal CNS might increase the overall myelin content of the corpus collosum and spinal cord. To investigate this possibility we performed an analysis of MBP expression in the corpus collosum and spinal cord over the course of pregnancy and the postpartum period by Western Blot. Remarkably, the expression levels of the 18, 17.2, and 14 kDa isoforms of MBP were significantly increased at both P7 and P14 relative to virgins (FIG. 11H-P; one-way ANOVA with Dunnett posthoc test; n=4). This result was not simply due to differences in age, as no increase in MBP expression was observed in the CC and SC of 6 week versus 12 week old adult virgin females. Therefore, the myelin content of the maternal CNS increases during the postpartum period, which parallels the timepoint at which new oligodendrocytes attain a mature complement of GSTit+ processes. Fully mature oligodendrocytes are unable to contribute to remyelination in the CNS and the process of myelin repair depends upon increased OPC proliferation and the generation of new oligodendrocytes.

EXAMPLE 8

Prolactin-Induced Oligodendrocytes Aid in Remyelination

Figure 12:
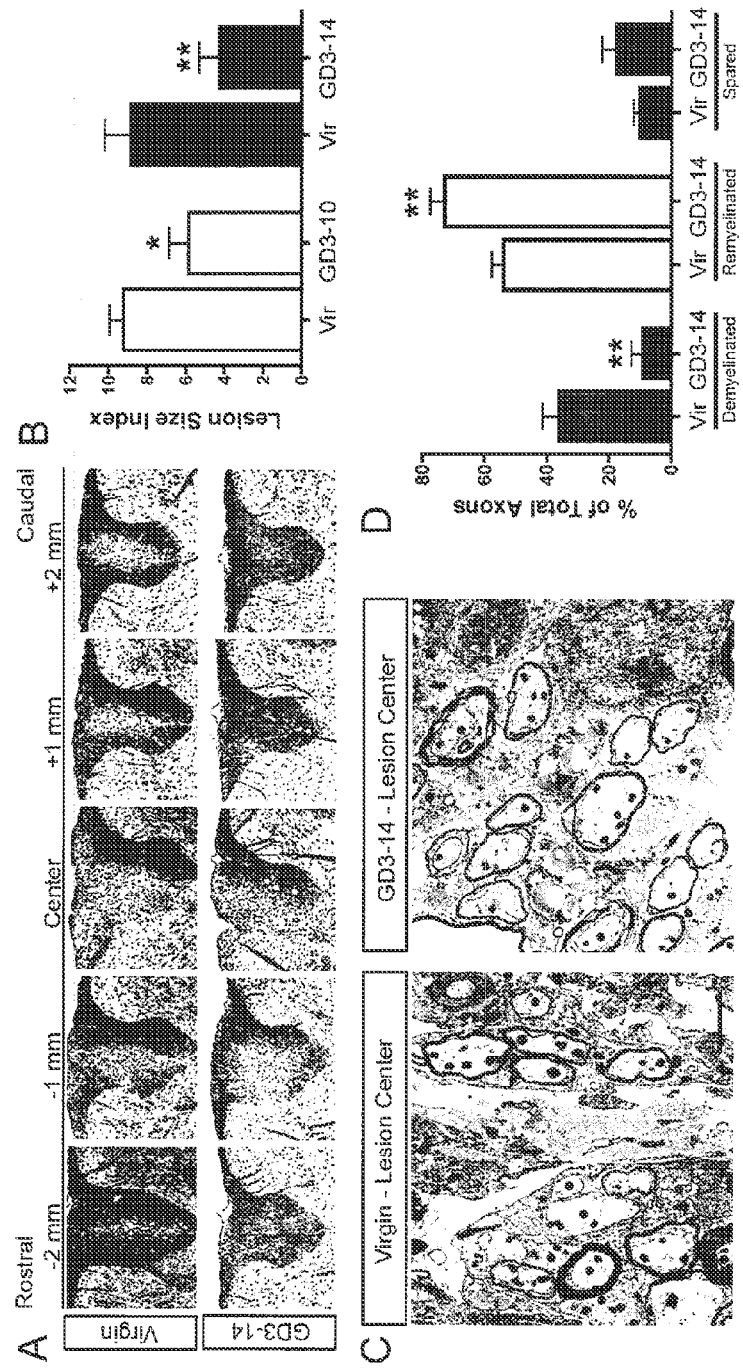
FIG. 12 shows that the pregnancy-induced increase in OPC proliferation and oligodendrocyte generation is associated with an enhanced capacity to remyelinate the maternal CNS.

Virgin and GD3 pregnant females received dorsal column lysolecithin lesions and were sacrificed 7 and 11 days later to assess the proportion of the dorsal column that remained lesioned (FIGS. 12A and B). For each animal, thirty-six serial sections taken through a 4 mm segment of the spinal cord (2 mm caudal and 2 mm rostral of the injection site) were stained with the myelin specific stain Luxol fast blue. The demyelinated area was quantified and normalized to the area of the dorsal column to provide an index of the lesion volume within the 4 mm SC segment of each animal (see Materials and Methods). In the pregnant GD3-10 animals, the volume of the lesion was decreased in size by 37% relative to matched virgin controls ($p<0.05$; unpaired t-test; $n=4$). By GD14, the lesion volume in the pregnant GD3-14 ($n=8$) animals was 52% smaller than that of matched virgin controls ($p<0.01$; unpaired t-test; $n=6$).

Electron microscopy was used to count the relative numbers of axons that were demyelinated, remyelinated, or spared within the lesion center of virgin versus GD3-14 females (FIGS. 12C and D). Relative to virgin controls, GD3-14 pregnant animals had 75% fewer demyelinated axons ($p<0.01$; unpaired t-test; $n=4$), a 35% increase in the proportion of remyelinated axons ($p<0.01$; unpaired t-test; $n=4$), but no significant change in the number of spared axons. Together, these results strongly suggest the pregnancy-induced increase in OPC proliferation and oligodendrocyte generation is associated with an enhanced capacity to remyelinate the maternal CNS.

EXAMPLE 9

Prolactin Promotes Oligodendrocyte Proliferation in Non-Pregnant Adult Mammals

Figure 13:
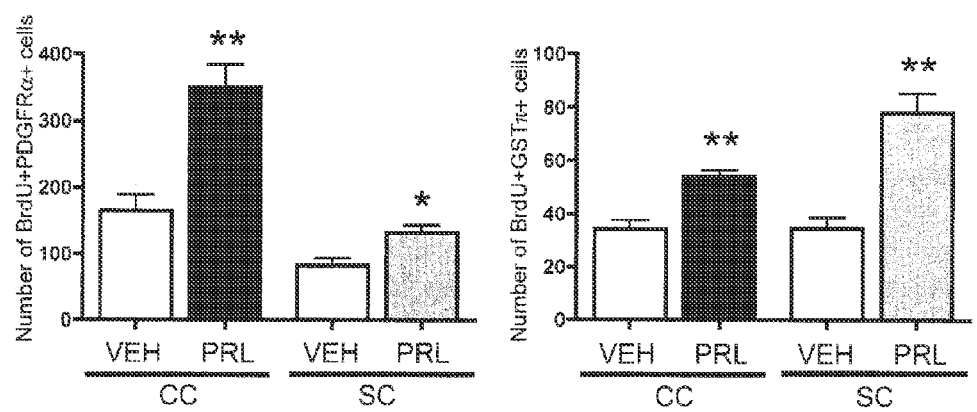
FIG. 13 shows that administration of prolactin alone is sufficient to promote oligodendrocyte proliferation in non-pregnant adult mammals.

To test whether PRL promotes OPC proliferation and the generation of new oligodendrocytes in the adult CNS, virgin female mice were infused with a vehicle control (VEH) or PRL subcutaneously for 3 days and delivered BrdU injections on the final day of the infusion. Relative to VEH controls, PRL infusions induced a 114% ($p<0.01$; unpaired-test; $n=5$) and 57% ($p<0.05$; unpaired t-test; $n=5$) increase in the number of dividing OPCs (BrdU+PDGFRa+ cells) in the CC and SC, respectively (FIG. 13A). Further, PRL infusions increased the generation of new oligodendrocytes (BrdU+GST^-t-cells) in both the corpus collosum and superior colliculus by 55% ($p<0.01$; unpaired t-test; $n=5$) and 124% ($p<0.01$; unpaired t-test; $n=5$), respectively (FIG. 13B). Similar to virgin females, PRL infusions also significantly increased OPC proliferation and the generation of new oligodendrocytes in the corpus collosum of adult males (Table 3). As was the case for pregnancy, the increases were due to increased OPC proliferation since PRL infusions did not alter cell survival as demonstrated by the absence of any change in the number of activated caspase-3+ cells within the corpus collosum of PRL versus VEH infused animals.

TABLE 3

| Number of immunoreactive cells in the corpus collosum of adult males | | |
|---|---|---|
| Marker | VEH | PRL |
| BrdU + PDGFRalpha | 384 ± 40 | 756 ± 58*** |
| BrdU + GSTpi(12 day BrdU trace) | 70 ± 4 | 95 ± 13* |

A number of embodiments of the invention have been described. Nevertheless, it will be understood that various modifications may be made without departing from the spirit and scope of the invention. Accordingly, other embodiments are within the scope of the following claims.

What is claimed is:

1. A method for reducing a symptom of a demyelinating disease in a subject, the method comprising selecting a subject with or suspected of having a demyelinating disease, and administering to the subject an effective amount of a prolactin or a prolactin releasing peptide.

2. The method of claim 1, wherein the demyelinating disease is multiple sclerosis.

3. The method of claim 1, further comprising administering to the subject a biological agent selected from the group consisting of epidermal growth (EGF), fibroblast growth factor (FGF), transforming growth factor alpha (TGFα), ciliary neurotrophic factor (CNTF), leukemia inhibitory factor (LIF), platelet-derived growth factor (PDGF), estrogen, ovarian hormone, human chorionic gonadotropin (hCG), insulin-like growth factor-1, and triiodothyrionine.

4. The method of claim 3, wherein the biological agent is hCG.

5. The method of claim 3, wherein the biological agent is PDGF.

6. The method of claim 3, wherein the biological agent is administered before the prolactin or prolactin releasing peptide.

7. The method of claim 3, wherein the biological agent is administered after the prolactin or prolactin releasing peptide.

8. The method of claim 3, wherein the biological agent is administered before and after the prolactin or prolactin releasing peptide.

9. A method of reducing a symptom of a disease or condition associated with demyelination in a subject, the method comprising selecting a subject with or suspected of having a disease or condition associated with demyelination and administering to the subject an effective amount of a prolactin or a prolactin releasing peptide.

10. The method of claim 9, wherein the disease or condition associated with demyelination is selected from the group consisting of multiple sclerosis, acute disseminated encephalomyelitis, diffuse cerebral sclerosis, necrotizing hemorrhagic encephalitis, leukodystrophies, stroke, spinal cord injury, bipolar disorder, acute brain injury, and dementia.

11. The method of claim 9, further comprising administering to the subject a biological agent selected from the group consisting of epidermal growth (EGF), fibroblast growth factor (FGF), transforming growth factor alpha (TGFα), ciliary neurotrophic factor (CNTF), leukemia inhibitory factor (LIF), platelet-derived growth factor (PDGF), estrogen, ovarian hormone, human chorionic gonadotropin (hCG), insulin-like growth factor-1, and triiodothyrionine.

12. The method of claim 11, wherein the biological agent is hCG.

13. The method of claim 11, wherein the biological agent is PDGF.

14. The method of claim 11, wherein the biological agent is administered before the prolactin or prolactin releasing peptide.

15. The method of claim 11, wherein the biological agent is administered after the prolactin or prolactin releasing peptide.

16. The method of claim 11, wherein the biological agent is administered before and after the prolactin or prolactin releasing peptide.

* * * * *